United States Patent
Hester, Jr. et al.

(10) Patent No.: US 6,927,229 B2
(45) Date of Patent: Aug. 9, 2005

(54) DIFLUOROTHIOACETAMIDES OF OXAZOLIDINONES AS ANTIBACTERIAL AGENTS

(75) Inventors: Jackson Boling Hester, Jr., Galesburg, MI (US); Wade J. Adams, Kalamazoo, MI (US); Jeffrey Charles Stevens, Kalamazoo, MI (US); Mikhail Fedor Gordeev, Castro Valley, CA (US); Upinder Singh, Freemont, CA (US); Carole Scott, Newark, CA (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 0 days.

(21) Appl. No.: 10/462,412

(22) Filed: Jun. 16, 2003

(65) Prior Publication Data

US 2004/0077626 A1 Apr. 22, 2004

Related U.S. Application Data

(60) Provisional application No. 60/392,213, filed on Jun. 28, 2002.

(51) Int. Cl.[7] .................. C07D 413/10; C07D 417/10; A61K 31/422; A61K 31/541; A61P 31/04
(52) U.S. Cl. .............. 514/376; 548/232; 540/544; 544/60
(58) Field of Search .................. 549/232; 514/376

(56) References Cited

U.S. PATENT DOCUMENTS

| | | | |
|---|---|---|---|
| 6,166,056 A | 12/2000 | Thomas et al. .......... | 514/376 |
| 6,281,210 B1 | 8/2001 | Hester, Jr. ............... | 514/235.8 |
| 6,342,513 B1 | 1/2002 | Hester, Jr. et al. ....... | 514/326 |
| 6,342,523 B1 | 1/2002 | Waterbury et al. ....... | 514/529 |

FOREIGN PATENT DOCUMENTS

| | | |
|---|---|---|
| WO | WO 01/46185 A1 | 12/2000 |
| WO | WO 01/58885 A1 | 2/2001 |
| WO | WO 01/98297 A2 | 6/2001 |

Primary Examiner—Mark L. Berch
Assistant Examiner—Kahsay Habte
(74) Attorney, Agent, or Firm—Lucy X. Yang

(57) ABSTRACT

The present invention describes difluororthioacetamide oxazolidinones of formula I:

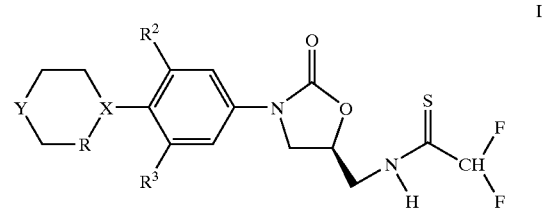

R is —$CH_2$— or —$CH_2CH_2$—; $R^2$ and $R^3$ are independently —H or —F; X is —CH—; Y is —SO—, —$SO_2$—, or —$SONR^4$—; and $R^4$ is —H or —$C_{1-4}$alkyl. These compounds are useful to treat infectives diseases caused by gram-positive and gram-negative bacteria.

24 Claims, No Drawings

DIFLUOROTHIOACETAMIDES OF OXAZOLIDINONES AS ANTIBACTERIAL AGENTS

CROSS REFERENCE

This application claims the benefit of the following provisional application: U.S. Ser. No. 60/392,213, filed Jun. 28, 2002, under 35 USC 119(e)(i), which is incorporated herein by reference in its entirety.

FILED OF THE INVENTION

The present invention describes difluororthioacetamide oxazolidinones as novel antibacterial agents, and antimicrobial combination therapies for combating infective diseases caused by gram-positive and gram-negative bacteria.

BACKGROUND OF THE INVENTION

The thioamide oxazolidinone antibacterial agents are a novel synthetic class of antimicrobials with broad activity against a number of human and veterinary pathogens, including gram-positive aerobic bacteria such as multiply-resistant staphylococci and streptococci, gram-negative aerobic bacteria such as *H. influenzae* and *M. catarrahlis*, as well as anaerobic organisms such as bacteroides and clostridia species, and acid-fast organisms such as *Mycobacterium tuberculosis* and *Mycobacterium aviur*.

As a chemical compound class, thioamide oxazolidinones generally are rapidly metabolized. It is known in the pharmaceutical filed that compounds with minimum metabolism are preferred to rapidly metabolized compounds for several reasons. It is easier to maintain therapeutic blood levels of slowly metabolized compounds (active ingredients) since they typically have lower clearance than rapidly metabolized compounds. Blood levels in humans are more predictable for slowly metabolized compounds since there is no effect from normal human variability in enzyme levels and activity. Metabolized compounds may also generate toxic metabolites, whereas non-metabolized compounds do not.

Accordingly, there is a demand to discover thioamide oxazolidinone antibacterial agents that possess minimum metabolism. Difluorothioacetamide oxazolidinones of the present invention have potent activity against gram-positive human and veterinary pathogens. In particular, it is unexpectedly discovered that these compounds have good stability in vivo and a very low metabolism rate.

INFORMATION DISCLOSURE

U.S. Pat. No. 6,342,513 discloses Oxazolidinone antibacterial agents having a thiocarbonyl functionality.

U.S. Pat. No. 6,281,210 discloses Benzoic acid esters of oxazolidinones having a hydroxyacetylpiperazine substituent.

U.S. Pat. No. 6,166,056 discloses phenyloxazolidinones having a C—C bond to 4–6 membered heterocyclic rings.

International publication WO 01/58885 discloses oxazolidinone thioamides with piperazine amide substituents.

International Publication WO 01/46185 discloses oxazolidinones having a sulfoximine functionality.

SUMMARY OF THE INVENTION

The present invention provides a novel oxazolidinone compound of formula I

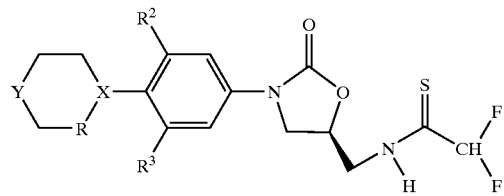

or pharmaceutically acceptable salt wherein
R is —CH$_2$— or —CH$_2$CH$_2$—;
R$^2$ and R$^3$ are independently —H or —F;
X is —N— or —CH—;
Y is —SO—, —SO$_2$—, or —SONR$^4$—; and R$^4$ is —H or —C$_{1-4}$alkyl.

The present invention further provides a method for treating gram-positive bacterial infections which comprises administration to a mammal being treated a pharmaceutically effective amount of the compound of formula I, either individually, or in combination with other gram-positive antibiotics.

The present invention further provides a method for treating gram-positive and gram-negative bacterial infections which comprises administration to a mammal being treated a pharmaceutically effective amount of the compound of formula I in combination with at least one other gram-negative antibiotic.

The present invention further provides compositions for treating gram-positive bacterial infections wherein the compositions comprise a pharmaceutically effective amount of the compound of formula I and at least one other gram-positive antibiotic.

The present invention further provides compositions for treating gram-positive and gram-negative bacterial infections wherein the compositions comprise a pharmaceutically effective amount of the compound of formula I and at least one other gram-negative antibiotic.

The present invention further provides methods of preparation of the compounds of formula I of the present invention.

The present invention further provides a use of the compound of formula I to prepare a medicament, for treating gram-positive and/or gram-negative bacterial infections.

DETAILED DESCRIPTION OF THE INVENTION

Definitions

The term "antibiotic" refers to an antibacterial agent other than the compound of the present invention.

Specifically, they refer to Amikacin, Gentamicin, Spectinomycin, Tobramycin, Imipenem, Meropenem, Cefadroxil, Cefazolin, Cephalexin, Cefaclor, Cefotetan, Cefoxitin, Cefprozil, Cefuroxime, Loracarbef, Cefdinir, Cefixime, Cefoperazone, Cefotaxime, Cefpodoxime, Ceftazidime, Ceftibuten, Ceftozoxime, Ceftriaxone, Cefepime, Azithromycin, Clarithromycin, Dirithromycin, Penicillin G, Cloxacillin, Dicloxacillin, Nafcillin, Oxacillin, Amoxicillin, Amoxicillin, Ampicillin, Mezlocillin, Piperacillin, Nalidixic Acid, Ciprofloxacin, Enoxacin, Lomefloxacin, Norfloxacin, Ofloxacin, Levofloxacin, Sparfloxacin, Alatrofloxacin, Gatifloxacin, Moxifloxacin, Trimethoprim, Sulfisoxazole, Sulfamethoxazole, Doxycycline, Minocycline, Tetracycline, Aztreonam, Chloramphenicol, Clindamycin, Quinupristin, Fosfomycin, Metronidazole, Nitrofurantoin, Rifampin, Trimethoprim, and Vancomycin. All of them are known. They can be either obtained commercially or be prepared according to the references cited in PHYSICIANS' DESK REFERENCE, the 53$^{rd}$ Edition (1999) and the US FDA's Orange book.

The term "gram-positive antibiotic" refers to an antibacterial agent active against gram-positive bacterial organisms.

The term "gram-negative antibiotic" refers to an antibacterial agent active against gram-negative bacterial organisms.

For the purpose of the present invention, the carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, the term "$C_{1-4}$alkyl refers to alkyl of one to four carbon atoms, inclusive, or methyl, ethyl, propyl, and butyl, straight and branched forms thereof.

Specifically, $R^2$ and $R^3$ are H.

Specifically, $R^2$ and $R^3$ are F.

Specifically, $R^2$ is H and $R^3$ is F.

Specifically, $R^2$ is F and $R^3$ is H.

Specifically, R is —CH$_2$—.

Specifically, R is —CH$_2$CH$_2$—.

Specifically, X is N.

Specifically X is CH.

Specifically Y is —SO—, or —SO$_2$—.

Specifically Y is —SO(NH)—.

Specifically Y is —SO(NCH$_3$)—.

Specifically Y is —SO(NHC$_{1-4}$alkyl)—.

Specifically, the formula I is the formula Ia or Ib shown below.

Ia

Ib

Specifically, the formula I is the formula Ic or Id shown below.

Ic

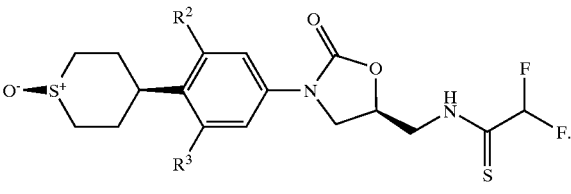

Id

Examples of the present invention are:
(1) 2,2-difluoro-N-[((5S)-3-{3-fluoro-4-[1-(methylimino)-1-oxido-1λ$^4$, 4-thiazinan-4-yl]phenyl}-2-oxo-1,3-oxazolidin-5-yl)methyl]ethanethioamide,
(2) 2,2-difluoro-N-({(5S-)-3-[3-fluoro-4-(1-imino-1-oxidohexahydro-1λ$^4$-thiopyran-4-yl)phenyl]-2-oxo-1,3-oxazolidin-5-yl}methyl)ethanethioamide (Z-(isomer),
(3) 2,2-difluoro-N-({(5S)-3-[3-fluoro-4-(1-imino-1-oxidohexahydro-1λ$^4$-thiopyran-4-yl)phenyl]-2-oxo-1,3-oxazolidin-5-yl}methyl)ethanethioamide (E-isomer),
(4) 2,2-difluoro-N-({(5S)-3-[3-fluoro-4-(1-methylimino-1-oxidohexahydro-1λ$^4$-thiopyran-4-yl)phenyl]-2-oxo-1,3-oxazolidin-5-yl}methyl)ethanethioamide (Z-isomer),
(5) 2,2-difluoro-N-({(5S)-3-[3-fluoro-4-(1-methylimino-1-oxidohexahydro-1λ$^4$-thiopyran-4-yl)phenyl]-2-oxo-1,3-oxazolidin-5-yl}methyl)ethanethioamide (E-isomer),
(6) 2,2-difluoro-N-({(5S)-3-[4-(1,1-dioxidothiomorpholin-4-yl)-3-fluorophenyl]-2-oxo-1,3-oxazolidin-5-yl}methyl)ethanethioamide,
(7) 2,2-difluoro-N-({(5S)-3-[4-(1,1-dioxidotetrahydro-2H-thiopyran-4-yl)-3-fluorophenyl]-2-oxo-1,3-oxazolidin-5-yl}methyl)ethanethioamide,
(8) 2,2-difluoro-N-({(5S)-3-[3-fluoro-4-(1-oxidotetrahydro-2H-thiopyran-4-yl)phenyl]-2-oxo-1,3-oxazolidin-5-yl}methyl)ethanethioamide (Z-Isomer),
(9) 2,2-difluoro-N-({(5S)-3-[3-fluoro-4-(1-oxidothiomorpholin-5-yl)phenyl]-2-oxo-1,3-oxazolidin-5-yl}methyl)ethanethioamide,
(10) 2,2-difluoro-N-({(5S)-3-[4-(1,1-dioxido-1,4-thiazepan-4-yl)-3-fluorophenyl]-2-oxo-1,3-oxazolidin-5-yl}methyl)ethanethioamide,
(11) 2,2-difluoro-N-({(5S)-3-[4-(1,1-dioxido-1,4-thiazepan-4-yl)phenyl]-2-oxo-1,3-oxazolidin-5-yl}methyl)ethanethioamide,
(12) 2,2-difluoro-N-({(5S)-3-[4-(1,1-dioxidothiomorpholin-4-yl)-3,5-difluorophenyl]-2-oxo-1,3-oxazolidin-5-yl}methyl)ethanethioamide,
(13) 2,2-difluoro-N-({(5S)-3-[4-(1,1-dioxidotetrahydro-2H-thiopyran-4-yl)-3,5-difluorophenyl]-2-oxo-1,3-oxazolidin-5-yl}methyl)ethanethioamide,
(14) 2,2-difluoro-N-({(5S)-3-[3,5-difluoro-4-(1-oxidothiomorpholin-4-yl)phenyl]-2-oxo-1,3-oxazolidin-5-yl}methyl)ethanethioamide,
(15) 2,2-difluoro-N-({(5S-3-[4-(1,1-dioxido-1,4-thiazepan-4-yl)-3,5-difluorophenyl]-2-oxo-1,3-oxazolidin-5-yl}methyl)ethanethioamide,
(16) 2,2-difluoro-N-({(5S)-3-[4-(1,1-dioxidothiomorpholin-4-yl)phenyl]-2-oxo-1,3-oxazolidin-5-yl}methyl)ethanethioamide,
(17) 2,2-difluoro-N-({(5S)-3-[4-(1-oxidothiomorpholin-4-yl)phenyl]-2-oxo-1,3-oxazolidin-5-yl}methyl)ethanethioamide,
(18) 2,2-difluoro-N-({(5S)-3-[3-fluoro-4-(1-imino-1-oxido-1λ$^4$, 4-thiazinan-4-yl)phenyl]-2-oxo-1,3-oxazolidin-5-yl}methyl)ethanethioamide,
(19) 2,2-difluoro-N-({(5S)-3-[3-fluoro-4-(1-oxido-1,4-thiazepan-4-yl)phenyl]-2-oxo-1,3-oxazolidin-5-yl}methyl)ethanethioamide,

(20) 2,2-difluoro-N-({(5S)-3-[4-(1-imino-1-oxido-1λ$^4$, 4-thiazinan-4-yl)phenyl]-2-oxo-1,3-oxazolidin-5-yl}methyl)ethanethioamide,
(21) 2,2-difluoro-N-(((5S)-3-{4-[1-(methylimino)-1-oxido-1λ$^4$, 4-thiazinan-4-yl]phenyl}-2-oxo-1,3-oxazolidin-5-yl)methyl]ethanethioamide,
(22) 2,2-difluoro-N-({(5S)-3-[3-fluoro-4-(1-oxidotetrahydro-2H-thiopyran-4-yl)phenyl]-2-oxo-1,3-oxazolidin-5-yl}methyl)ethanethioamide (E-Isomer),
(23) 2,2-difluoro-N-({(5S)-3-[4-(1,1-dioxidotetrahydro-2H-thiopyran-4-yl)phenyl]-2-oxo-1,3-oxazolidin-5-yl}methyl)ethanethioamide,
(24) 2,2-difluoro-N-({(5S)-3-[4-(1-oxidotetrahydro-2H-thiopyran-4-yl)phenyl]-2-oxo-1,3-oxazolidin-5-yl}methyl)ethanethioamide (Z-isomer),
(25) 2,2-difluoro-N-({(5S)-3-[3,5-difluoro-4-(1-oxidotetrahydro-2H-thiopyran-4-yl)phenyl]-2-oxo-1,3-oxazolidin-5-yl}methyl)ethanethioamide (E-isomer),
(26) 2,2-difluoro-N-({(5S)-3-[4-(1-oxidotetrahydro-2H-thiopyran-4-yl)phenyl]-2-oxo-1,3-oxazolidin-5-yl}methyl)ethanethioamide (E-isomer),
(27) 2,2-difluoro-N-({(5S)-3-[3,5-difluoro-4-(1-oxidotetrahydro-2H-thiopyran-4-yl)phenyl]-2-oxo-1,3-oxazolidin-5-yl}methyl)ethanethioamide (Z-isomer),
(28) 2,2-difluoro-N-({(5S)-3-[4-(1-imino-1-oxidohexahydro-1λ$^4$-thiopyran-4-yl)phenyl]-2-oxo-1,3-oxazolidin-5-yl}methyl)ethanethioamide (Z-isomer),
(29) 2,2-difluoro-N-({(5S)-3-[4-(1-imino-1-oxidohexahydro-1λ$^4$-thiopyran-4-yl)phenyl]-2-oxo-1,3-oxazolidin-5-yl}methyl)ethanethioamide (E-isomer),
(30) 2,2-difluoro-N-({(5S)-3-[4-(1-methylimino-1-oxidohexahydro-1λ$^4$-thiopyran-4-yl)phenyl]-2-oxo-1,3-oxazolidin-5-yl}methyl)ethanethioamide (Z-isomer), and
(31) 2,2-difluoro-N-({(5S)-3-[4-(1-methylimino-1-oxidohexahydro-1λ$^4$-thiopyran-4-yl)phenyl]-2-oxo-1,3-oxazolidin-5-yl}methyl)ethanethioamide (E-isomer).

Descriptions for the Preparation

Compounds of formula I are prepared as illustrated in Schemes I and II. As shown in Scheme I compounds of formula I are conveniently prepared by allowing compounds of formula II to react with an ester of difluoroethanethioic O-acid (III) where R$^5$ is C$_{1-4}$ alkyl, optionally substituted by one or two phenyl groups. Suitable solvents for this reaction include methanol, chloroform, methylene chloride or mixtures thereof at temperatures of about 10° C. to about 30° C. A tertiary amine base can be used to facilitate this reaction, especially if a salt of the amine (II) is employed.

Alternatively, a compound of formula I can be obtained by reacting a compound of formula II with O-(3,3-diphenylpropyl)difuoroethanethioate in protic or aprotic polar solvents (such as methanol, acetonitrile, dioxane, methylene cloride (CH$_2$Cl$_2$), N,N-dimethylformamide, dimethylsulfoxide or alike, or mixtures thereof) in presence of an optional organic or inorganic base (such as triethylamine, pyridine, or potassium carbonate). The process can be conducted in the range of temperatures of 5–100 C., preferably, at 20–75 C.

A second method for the preparation of compounds of formula I (wherein Y' is —SO$_2$—, or —SONR$^4$—) is shown in Scheme II. In this method compounds of formula II' are condensed with difluoroacetic acid to give compounds of formula IV. Reagents and conditions for this condensation include the use of 1-(3-dimethylaminopropyl)-3-ethylcarbodiimide hydrochloride (EDC) with 4-(dimethylamino)pyridine (DMAP) in pyridine at about 0° C. to about 25° C.; or EDC with 1-hydroxybenzotriazole hydrate (HOBT) and triethylamine in DMF at 0° C. to 25° C. Compounds of formula IV are then allowed to react with Lawesson's Reagent in dioxane at temperatures of about 50° C. to about 100° C. to give compounds of formula I'.

Scheme I

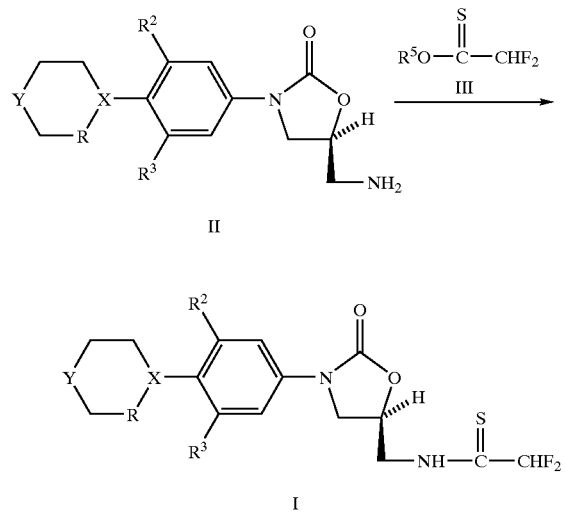

Scheme II

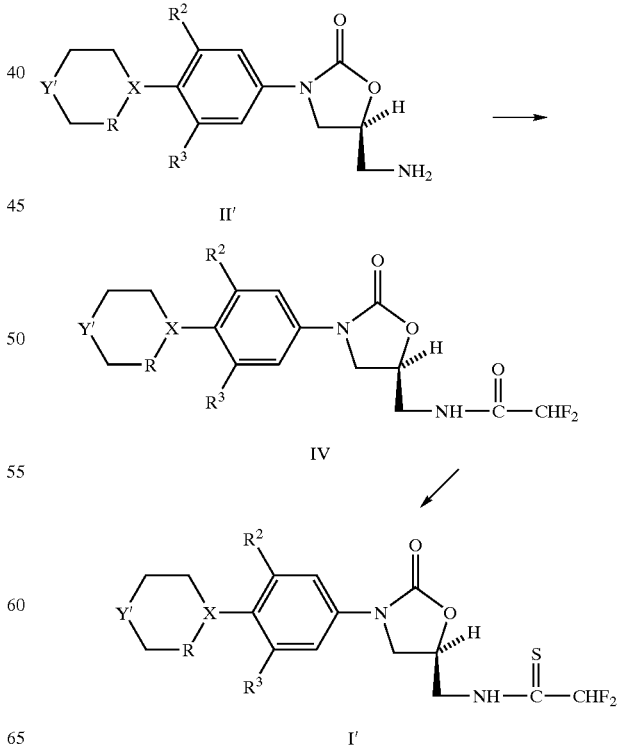

EXAMPLES

Example 1

Preparation of 2,2-difluoro-N-[((5S)-3-{3-fluoro-4-[1-(methylimino)-1-oxido-1$\lambda^4$, 4-thiazinan-4-yl]phenyl}-2-oxo-1,3-oxazolidin-5-yl)methyl]ethanethioamide (1)

Step 1.

Preparation of (5S)-5-(aminomethyl)-3-{3-fluoro-4-[1-(methylimino)-1-oxido-1$\lambda^4$,4-thiazinan-4-yl]phenyl}-1,3-oxazolidin-2-one (3)

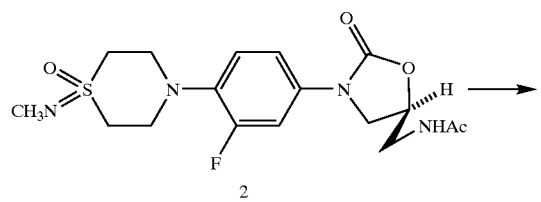

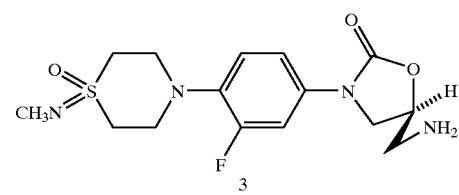

A stirred solution of 2 (prepared according to the procedure described in International Publication WO 01/46185) (100 mg, 0.25 mmol) in MeOH (7 ml) is treated with water (1 ml) and concentrated hydrochloric acid (1 ml), refluxed for 17 hours and concentrated in vacuo. A mixture of the residue and brine is adjusted to pH 11 with sodium hydroxide and extracted with 5% MeOH—CH$_2$Cl$_2$. The extracts are dried (Na$_2$SO$_4$) and concentrated. Flash chromatography of the residue on silica gel with 10% MeOH—0.05% NH$_4$OH—CHCl$_3$ gave the title compound (3). MS (ESI+) m/z 357 (M+H$^+$); MS (ESI−) m/z 391 (M+Cl)

Step 2.

Preparation of 2,2-difluoro-N-[((5S)-3-{3-fluoro-4-[1-(methylimino)-1-oxido-1$\lambda^4$,4-thiazinan-4-yl]phenyl}-2-oxo-1,3-oxazolidin-5-yl)methyl]acetamide (4)

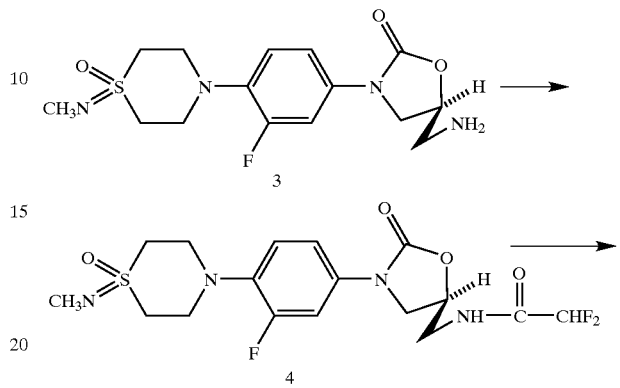

A stirred mixture of 3 (518 mg, 1.45 mmol), difluoroacetic acid (107 μL, 1.74 mmol), 1-(3-dimethylaminopropyl)-3-ethylcarbodiimide hydrochloride (EDC) (340 mg, 1.77 mmol), 4-(dimethylamino)pyridine (DMAP) (18 mg, 0.15 mmol) and pyridine (10 ml) is kept, under nitrogen at ambient temperature (24° C.) for 24 hours, treated with additional difluoroacetic acid (107 μL) and EDC (350 mg) and stirred for about 96 hours. It is diluted with MeOH and concentrated in vacuo. A mixture of the residue and brine is adjusted to pH 11 with 1N NaOH and extracted with 5% MeOH—CH$_2$Cl$_2$. The extract is dried (NaSO$_4$) and concentrated. Flash chromatography of the residue on silica gel with 3% MeOH—CH$_2$Cl$_2$ gave the title compound (4). MS (ESI+) m/z 435 (M+H$^+$); MS (ESI−) m/z 433 (M−H), 469 (M+Cl); HRMS (ESI) calcd for C$_{17}$H$_{22}$F$_3$N$_4$O$_4$S (M+H$^+$) 435.1313, found 435.1325

Step 3.

Preparation of 2,2-difluoro-N-[((5S)-3-{3-fluoro-4-[1-(methylimino)-1-oxido-1$\lambda^4$, 4-thiazinan-4-yl]phenyl}-2-oxo-1,3-oxazolidin-5-yl)methyl]ethanethioamide (1)

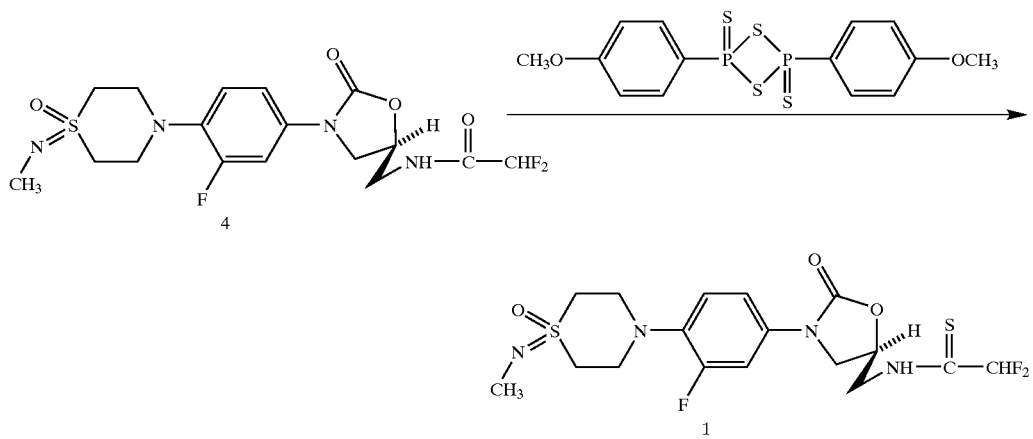

A stirred solution of 4 (324 mg, 0.746 mmol) in dioxane (10 ml) is treated, portionwise during 10 min, with Lawesson's Reagent (336 mg, 0.831 mmol) and refluxed, under nitrogen, for 2 hours. It is cooled, diluted with MeOH and $CH_2Cl_2$ and a concentrated in vacuo. A solution of the residue in $CH_2Cl_2$ is extracted first with 3N HCl and then with 1N HCl. The combined aqueous extract is neutralized to pH 6–7, concentrated in vacuo to about 150 ml, adjusted to pH 11–12 with 50% NaOH and extracted with 5% MeOH—$CH_2Cl_2$. The extract is dried ($Na_2SO_4$) and concentrated. Flash chromatography of the residue on silica gel with 1–2% MeOH—$CH_2Cl_2$ gave the title compound (1).

Physical data: MS (ESI+) m/z 451 (M+H$^+$), 473 (M+Na$^+$).

MS (ESI−) m/z 449 (M−H).

HRMS (FAB) calcd for $C_{17}H_{22}F_3N_4O_3S_2$ (M+H$^+$) 451.1085, found 451.1075.

Example 2

Preparation of 2,2-difluoro-N-({(5S—)-3-[3-fluoro-4-(1-imino-1-oxidohexahydro-1$\lambda^4$-thiopyran-4-yl)phenyl]-2-oxo-1,3-oxazolidin-5-yl}methyl)ethanethioamide, Z-isomer (5)

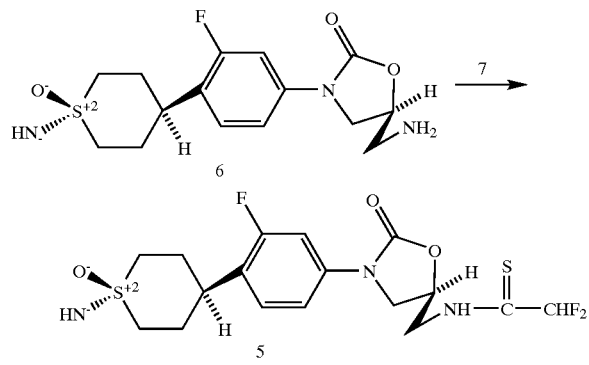

A stirred suspension of 6 (prepared according to the procedure described in International Publication WO 01/46185) (0.54 g, 1.23 mmol) in MeOH (5 ml) is treated dropwise with a solution of O-(3,3-diphenylpropyl) difluoroethanethioate 7 (0.43 g, 1.40 mmol) in $CH_2Cl_2$ (5 ml) and the resulting pale yellow solution is kept at ambient temperature (24° C.) for 40 min and concentrated in vacuo. Flash chromatography of the residue on silica gel with 3% MeOH—$CHCl_3$ and crystallization of the product from MeOH gave the title compound (5).

Physical data: mp 212–213° C. (dec).

MS (ESI+) m/z 436 (M+H$^+$).

MS (ESI−) m/z 434 (M−H).

Anal. Calcd for $C_{17}H_{20}F_3N_3O_3S_2$: C, 46.89: H, 4.63; N, 9.65. Found: C, 46.89; H, 4.65; N, 9.61.

Method for Preparing O-(3,3-diphenylpropyl) difluoroethanethioate 7:

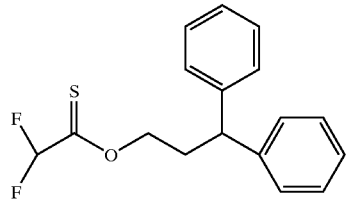

To a stirred solution of difluoroacetic acid (5.00 g, 52.1 mmol) and 3,3-diphenyl-1-propanol (11.4 ml, 57.3 mmol, 1.10 eq) in diethyl ether (100 ml) is added 4-dimethylaminopyridine (0.64 g, 5.21 mmol, 0.01 eq) followed by diisopropylcarbodiimide (6.56 g, 52.1 mmol, 1.0 eq). The mixture is stirred at room temperature overnight. The precipitate is removed by vacuum filtration and washed with ether and the filtrate concentrated in vacuo. The residue is filtered through a plug of silica gel using 5% ether/hexanes eluent and the filtrate collected and concentrated. The resulting compound (14.40 g, 46.64 mmol) in xylenes (150 ml) is added Lawesson's Reagent (24.1 g, 59.61 mmol). The reaction mixture is heated at reflux overnight and then cooled to room temperature. A precipitate formed which is removed by vacuum filtration and washed with ethyl acetate. The filtrate is passed through a plug of silica gel and eluted with 5% ether/hexanes and concentrated to give the title compound 7. $^1$H NMR (400 Mhz), CDCl$_3$) δ 2.47, 4.07, 4.24, 5.82, 7.23.

Example 3

Preparation of 2,2-difluoro-N-({(5S)-3-[3-fluoro-4-(1-imino-1-oxidohexahydro-1$\lambda^4$-thiopyran-4-yl)phenyl]-2-oxo-1,3-oxazolidin-5-yl}methyl)ethanethioamide, E-isomer (8)

Step 1.

Preparation of (5S)-5-(aminomethyl)-3-[3-fluoro-4-(1-imino-1-oxidohexahydro-1$\lambda^4$-thiopyran-4-yl)phenyl]-1,3-oxazolidin-2-one, E-isomer Hydrochloride (10)

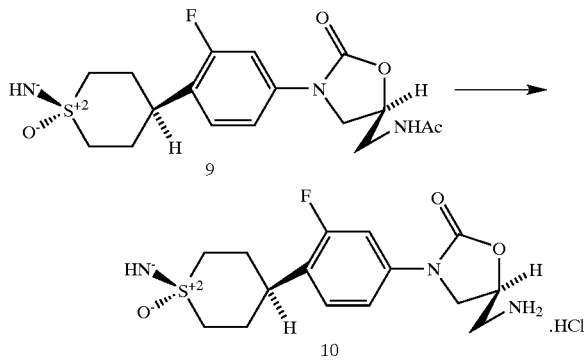

A solution of 9 (prepared according to the procedure described in International Publication WO 01/46185) (1.02 g, 2.66 mmol) in MeOH (35 ml) is treated with water (5 ml) and concentrated hydrochloric acid (5 ml) and refluxed for 24 hours. The mixture is concentrated in vacuo to give the title compound (10) as solid.

Step 2.

Preparation of 2,2-difluoro-N-({(5S)-3-[3-fluoro-4-(1-imino-1-oxidohexahydro-1λ4-thiopyran-4-yl)phenyl]-2-oxo-1,3-oxazolidin-5-yl}methyl)ethanethioamide, E-isomer (8)

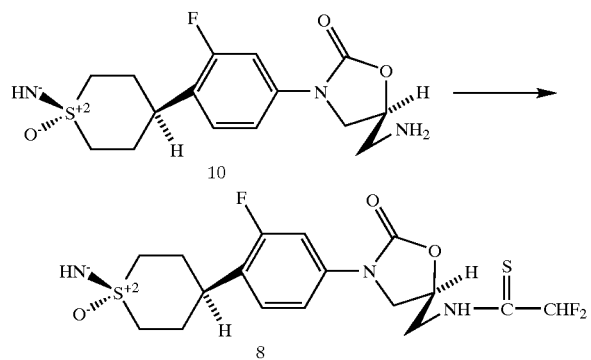

A stirred solution of 10 (0.55 g, 1.3 mmol), MeOH (7 ml), CH$_2$Cl$_2$ (7 ml) and triethylamine (0.37 ml, 2.7 mmol) is treated, dropwise with a solution of 7 (0.46 g, 1.5 mmol) in 1 ml of MeOH: CH$_2$Cl$_2$ (1:1) and stirred, under nitrogen at ambient temperature (24° C.) for 1 hour. It is then a concentrated in vacuo and the residue is flash chromatographed on silica gel with 3% MeOH—CHCl$_3$. Crystallization of the product from MeOH gave the title compound (8)

Physical data: mp 190–191° C.

MS (ESI+) m/z 436 (M+H$^+$).

MS (ESI−) m/z 434 (M−H).

Anal. Calcd for C$_{17}$H$_{20}$F$_3$N$_3$O$_3$S$_2$: C, 46.89; H, 4.63; N, 9.65. Found: C, 46.68; H, 4.64; N, 9.55.

Example 4

Preparation of 2,2-difluoro-N-({(5S)-3-[3-fluoro-4-(1-methylimino-1-oxidohexahydro-1λ4-thiopyran-4-yl)phenyl]-2-oxo-1,3-oxazolidin-5-yl}methyl)ethanethioamide, Z-isomer (11)

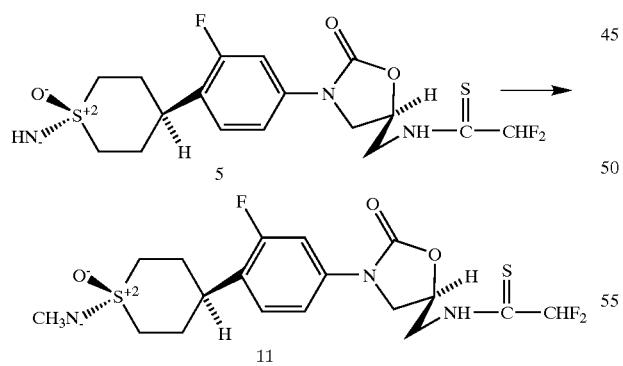

A stirred mixture of 5 (200 mg, 0.46 mmol) and paraformaldehyde (43 mg, 1.43 mmol) in CH$_3$CN (6 ml) is treated with trifluoroacetic acid (TFA) (142 μL, 1.83 mmol) and triethylsilane (220 μL, 1.38 mmol). It is kept at ambient temperature (24° C.), under nitrogen for 19 hours, diluted with brine and adjusted to pH 11 with 1 N NaOH. This mixture is extracted with 5% MeOH—CH$_2$Cl$_2$. The extract is dried (Na$_2$SO$_4$) and concentrated in vacuo. Chromatography of the residue on silica gel with 3% MeOH—CHCl$_3$ provides the title compound (11).

Physical data: MS (ESI+) m/z 450 (M+H$^+$).

MS (ESI−) m/z 448 (M−H).

HRMS (FAB) calcd for C$_{18}$H$_{23}$F$_3$N$_3$O$_3$S$_2$ (M+H$^+$) 450.1133, found 450.1130.

Example 5

Preparation of 2,2-difluoro-N-({(5S)-3-[3-fluoro-4-(1-methylimino-1-oxidohexahydro-1λ4-thiopyran-4-yl)phenyl]-2-oxo-1,3-oxazolidin-5-yl}methyl)ethanethioamide, E-isomer (12)

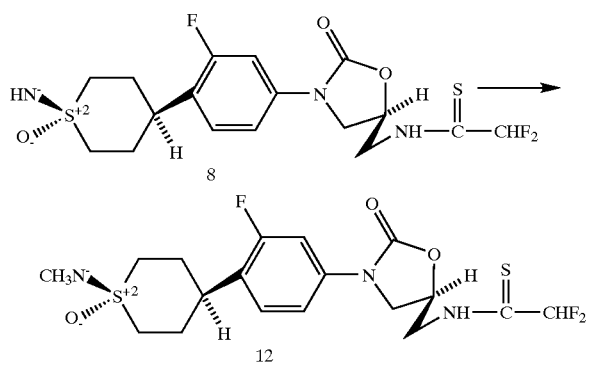

Following the procedure described in Example 4 for the preparation of 11, the reaction of 8 with paraformaldehyde, TFA and triethylsilane provides 12 which is purified by silica gel chromatography with 3.5% MeOH—CHCl$_3$.

Physical data: MS (ESI+) m/z 450 (M+H$^+$).

MS (ESI−) m/z 448 (M−H).

HRMS (FAB) calcd for C$_{18}$H$_{23}$F$_3$N$_3$O$_3$S$_2$ (M+H$^+$) 450.1133, found 450.1134.

Example 6

Preparation of 2,2-difluoro-N-({(5S)-3-[4-(1,1-dioxidothiomorpholin-4-yl)-3-fluorophenyl]-2-oxo-1,3-oxazolidin-5-yl}methyl)ethanethioamide (13). 2672

Step 1.

Preparation of N-({(5S)-3-[4-(1,1-dioxidothiomorpholin-4-yl)-3-fluorophenyl]-2-oxo-1,3-oxazolidin-5-yl}methyl)-2,2-difluoroacetamide (15)

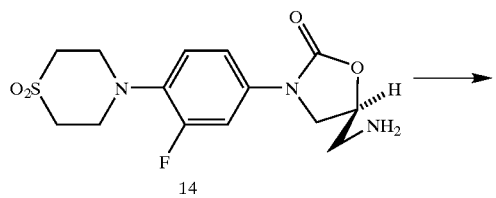

-continued

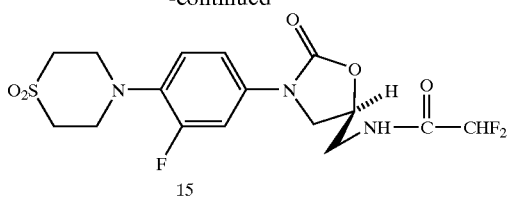

15

An ice cold, stirred mixture of 14 (prepared according to the procedure described in U.S. Pat. No. 6,342,523) (1.00 g, 2.91 mmol), HOBT (433 mg, 3.20 mmol) and difluoroacetic acid (0.275 ml, 4.37 mmol) in DMF (25 ml) is treated with EDC (1.23 g, 6.40 mmol) and kept in the ice bath for 2 hours and at ambient temperature (24° C.) for 3 days. It is concentrated in vacuo and the residue is stirred with water (80 ml) and filtered. The solid is washed with water and dried to give the title compound (15) as solid. A sample is chromatographed on silica gel with 2.5% MeOH—CH$_2$Cl$_2$ and crystallized from MeOH: mp 177–178° C.; MS (EI) m/z 421 (M$^+$). Anal calcd for C$_{16}$H$_{18}$F$_3$N$_3$O$_5$S: C, 45.60; H, 4.30; N, 9.97. Found: C, 45.56; H, 4.31; N, 9.97.

Step 2.

Preparation of 2,2-difluoro-N-({(5S)-3-[4-(1,1-dioxidothiomorpholin-4-yl)-3-fluorophenyl]-2-oxo-1,3-oxazolidin-5-yl}methyl)ethanethioamide (13)

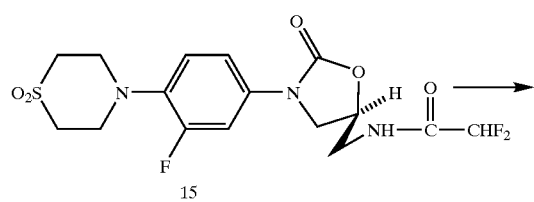

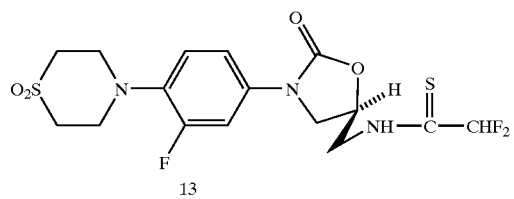

13

Following the procedure described in Example 1 for the preparation of 1 the reaction of 15 with Lawesson's Reagent provides the title compound (13), which is purified by silica gel chromatography with 2.5% MeOH—CH$_2$Cl$_2$ and crystallization from EtOAc-hexane.

Physical data: mp 146–147° C.

MS (EI) m/z 437.1 (M$^+$).

Anal calcd for C$_{16}$H$_{18}$F$_3$N$_3$O$_4$S$_2$: C, 43.93; H, 4.15; N, 9.60. Found: C, 43.79; H, 4.15; N, 9.55.

Example 7

Preparation of 2,2-difluoro-N-({(5S)-3-[4-(1,1-dioxidotetrahydro-2H-thiopyran-4-yl)-3-fluorophenyl]-2-oxo-1,3-oxazolidin-5-yl}methyl)ethanethioamide (16)

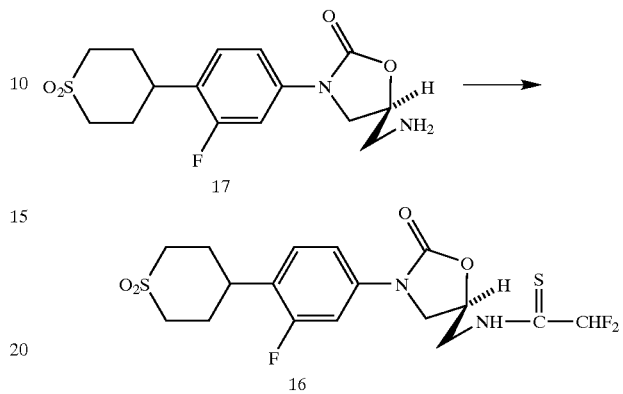

Following the procedure described in Example 6 for the preparation of 13 the amine 17, (prepared according to the procedure described in U.S. Pat. No. 6,342,523) is first condensed with difluoroacetic acid and the resulting amide is allowed to react with Lawesson's Reagent to give 16 which is purified by silica gel chromatography with 3% MeOH—CH$_2$Cl$_2$ and crystallization from CH$_2$Cl$_2$-hexane.

Physical data: mp 168–169° C.

MS (EI) m/z 436 (M$^+$).

Anal. calcd for C$_{17}$H$_{19}$F$_3$N$_2$O$_4$S$_2$: C, 46.78; H, 4.39; N, 6.42. Found: C, 46.85; H, 4.49; N, 6.32.

Example 8

Preparation of 2,2-difluoro-N-({(5S)-3-[3-fluoro-4-(1-oxidotetrahydro-2H-thiopyran-4-yl)phenyl]-2-oxo-1,3-oxazolidin-5-yl}methyl)ethanethioamide, Z-Isomer (18)

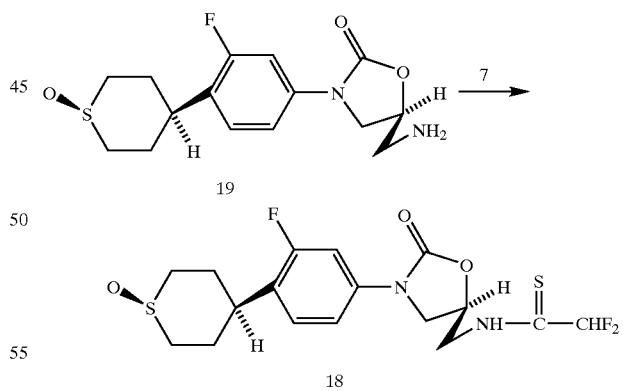

A stirred solution of 19 (prepared according to the procedure described in U.S. Pat. No. 6,342,523) (407.6 mg, 1.25 mmol) in CH$_2$Cl$_2$ (8 ml) is treated with a solution of 7 (420.8 mg, 1.37 mmol) in CH$_2$Cl$_2$ (2 ml) and kept at ambient temperature (24° C.) for 18 hours. It is then diluted with CH$_2$Cl$_2$, washed with saturated NaHCO$_3$, water, and brine, dried (MgSO$_4$) and concentrated.

Chromatography of the residue on silica gel with 2% MeOH—CH$_2$Cl$_2$ provides the title compound (18).

Physical data: mp 192–194° C.

Anal. calcd for $C_{17}H_{19}F_3N_2O_3S_2$: C, 48.56; H, 4.55; N, 6.66; S, 15.25. Fou C, 48.56; H, 4.61; N, 6.57; S, 14.83.

Example 9

Preparation of 2,2-difluoro-N-({(5S)-3-[3-fluoro-4-(1-oxidothiomorpholin-5-yl)phenyl]-2-oxo-1,3-oxazolidin-5-yl}methyl)ethanethioamide (18)

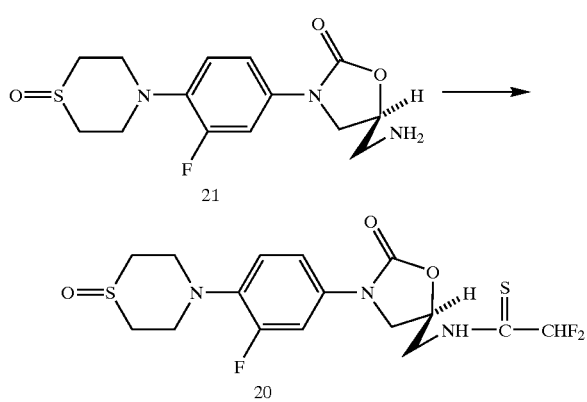

Following the procedure described in Example 8 for the preparation of 18 the reaction of 21 (prepared according to the procedure described in U.S. Pat. No. 6,342,523) with 7 provides the title compound 20.

Physical data: Anal. calcd for $C_{16}H_{18}F_3N_3O_3S_2$: C, 45.60; H, 4.30; N, 9.97.

Found: C, 45.73; H, 4.44; N, 9.74.

Example 10

Preparation of 2,2-difluoro-N-({(5S)-3-[4-(1,1-dioxido-1,4-thiazepan-4-yl)-3-fluorophenyl]-2-oxo-1,3-oxazolidin-5-yl}methyl)ethanethioamide (22)

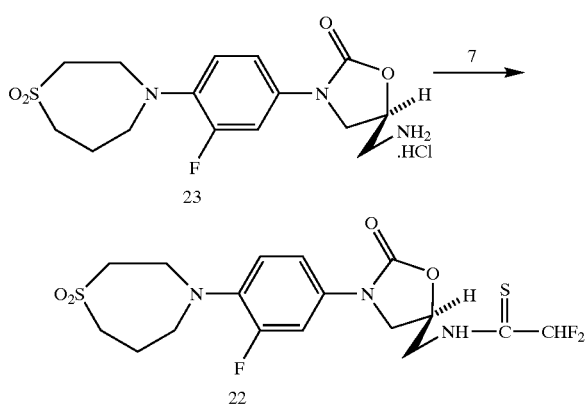

Following the procedure described in Example 3 for the preparation of 8, a stirred mixture of the amine hydrochloride (23) (prepared according to the procedure described in U.S. Pat. No. 6,342,523) and N,N-diisopropylethylamine in $CH_2Cl_2$ is allowed to react with 7 to give the title compound 22 which is purified by silica gel chromatography with 3% MeOH—$CH_2Cl_2$.

Physical data: mp 128–130° C.

Anal. calcd for $C_{17}H_{20}F_3N_3O_4S_2$: C, 45.22; H, 4.47; N, 9.31, S, 14.20. Found: C, 45.54; H, 4.53, N, 8.98; S, 13.69.

Example 11

Preparation of 2,2-difluoro-N-({(5S)-3-[4-(1,1-dioxido-1,4-thiazepan-4-yl)phenyl]-2-oxo-1,3-oxazolidin-5-yl}methyl)ethanethioamide (24)

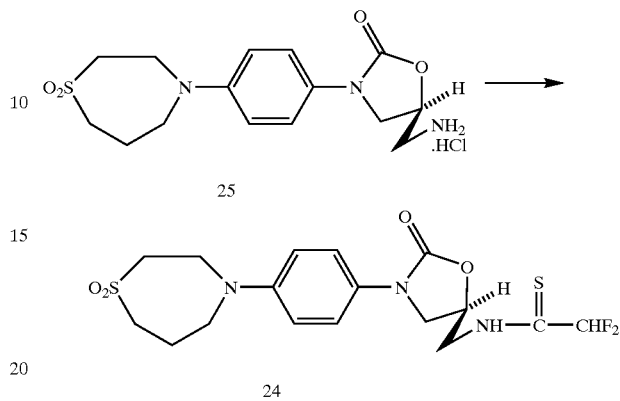

Following the procedure described In Example 10 for the preparation of 22, the reaction of 25 (prepared according to the procedure described in U.S. Pat. No. 6,342,523) with 7 provides the title compound 24.

Physical data: Anal. calcd for $C_{17}H_{21}F_2N_3O_4S_2$: C, 47.10; H, 4.88; N, 9.69; S, 14.79. Found: C, 47.26; H, 5.12; N, 9.27; S, 14.14.

Example 12

Preparation of 2,2-difluoro-N-({(5S)-3-[4-(1,1-dioxidothiomorpholin-4-yl)-3,5-difluorophenyl]-2-oxo-1,3-oxazolidin-5-yl}methyl)ethanethioamide (26)

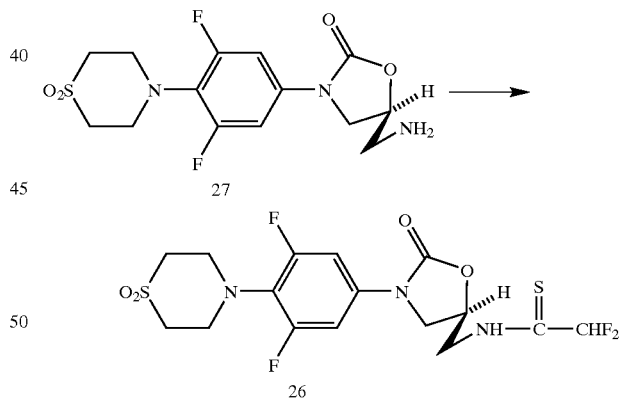

Following the procedure described in Example 6 for the preparation of 13 the amine 27 (prepared according to the procedure described in U.S. Pat. No. 6,342,523) is first condensed with difluoroacetic acid and the resulting amide is allowed to react with Lawesson's Reagent to give the title compound 26 which is purified by silica gel chromatography with 5% MeOH—$CH_2Cl_2$.

Physical data: mp 88–90° C.

HRMS (FAB) calcd for $C_{16}H_{18}F_4N_3O_4S_2$ (M+H$^+$) 456.0675, found 456.0671.

Anal. calcd for $C_{16}H_{17}F_4N_3O_4S_2$: C, 42.19; H, 3.76; N, 9.23. Found: C, 42.12; H, 3.93; N, 8.79.

Example 13

Preparation of 2,2-difluoro-N-({(5S)-3-[4-(1,1-dioxidotetrahydro-2H-thiopyran-4-yl)-3,5-difluorophenyl]-2-oxo-1,3-oxazolidin-5-yl}methyl)ethanethioamide (28)

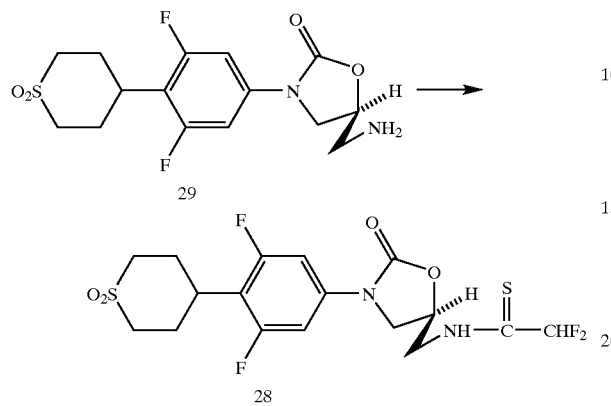

Following the procedure described in Example 9 for the preparation of 20 the reaction of 29 (prepared according to the procedure described in U.S. Pat. No. 6,342,523) with 7 provides the title compound 28.

Physical data: mp 126–128° C.

MS m/z 455 (M+H+).

Example 14

Preparation of 2,2-difluoro-N-({(5S)-3-[3,5-difluoro-4-(1-oxidothiomorpholin-4-yl)phenyl]-2-oxo-1,3-oxazolidin-5-yl}methyl)ethanethioamide (30)

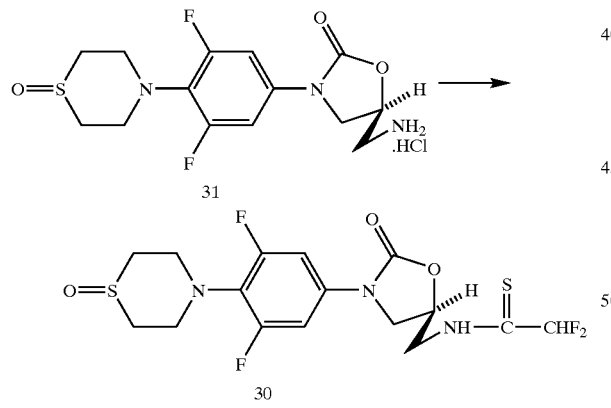

Following the procedure described in Example 3 for the preparation of 8, a mixture of 31 (prepared according to the procedure described in U.S. Pat. No. 6,342,523) and triethylamine in CH$_2$Cl$_2$ is allowed to react with 7 to give the title compound 30 which is purified by silica gel chromatography with 2% MeOH—CH$_2$Cl$_2$.

Physical data:

HRMS calcd for C$_{16}$H$_{18}$F$_4$N$_3$O$_3$S$_2$ (M+H+) 440.0725, found 440.0724.

Anal. calcd for C$_{16}$H$_{17}$F$_4$N$_3$O$_3$S$_2$: C, 43.73; H, 3.90; N, 9.56. Found: C, 43.99; H, 4.15; N, 9.31.

Example 15

Preparation of 2,2-difluoro-N-({(5S)-3-[4-(1,1-dioxido-1,4-thiazepan-4-yl)-3,5-difluorophenyl]-2-oxo-1,3-oxazolidin-5-yl}methyl)ethanethioamide (32)

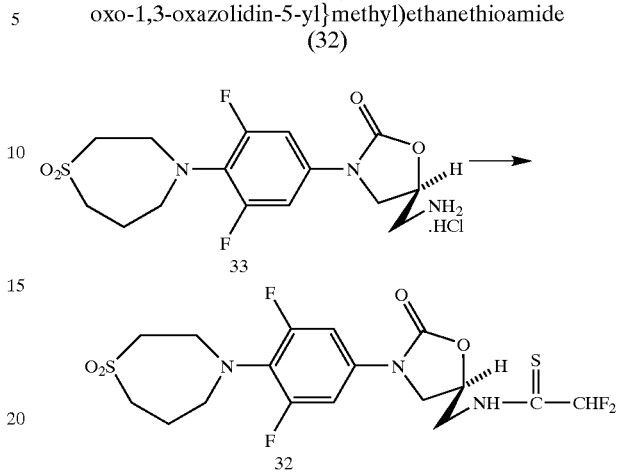

Following the procedure described in Example 3 for the preparation of 8, a mixture of 33 (prepared according to the procedure described in U.S. Pat. No. 6,342,523) and triethylamine in CH$_2$Cl$_2$ is allowed to react with 7 to give the title compound 32 which is purified by silica gel chromatography with 3% MeOH—CH$_2$Cl$_2$.

Physical data:

HRMS calcd for C$_{17}$H$_{20}$F$_4$N$_3$O$_4$S$_2$ (M+H+) 470.0831, found 470.0844.

Anal. calcd for C$_{17}$H$_{19}$F$_4$N$_3$O$_4$S$_2$: C, 43.49; H, 4.08; N, 8.95. Found: C, 43.70; H, 4.17; N, 8.86.

Example 16

Preparation of 2,2-difluoro-N-({(5S)-3-[4-(1,1-dioxidothiomorpholin-4-yl)phenyl]-2-oxo-1,3-oxazolidin-5-yl}methyl)ethanethioamide (34)

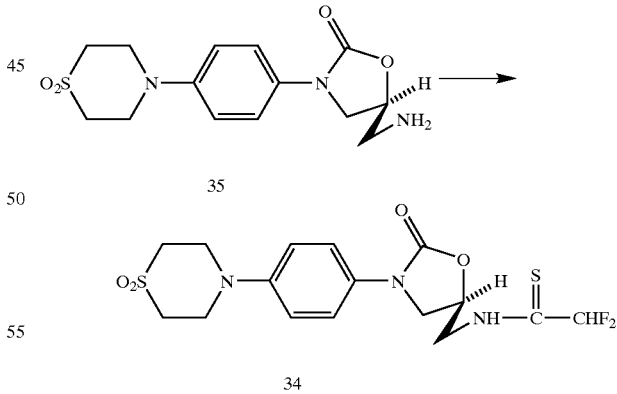

Following the procedure described in Example 3 for the preparation of 8, the amine 35 (prepared according to the procedure described in U.S. Pat. No. 6,342,523) is first condensed with difluoroacetic acid and the resulting amide is allowed to react with Lawesson's Reagent to give 34 which is purified by silica gel chromatography with 2% MeOH—CH$_2$Cl$_2$ and crystallization from EtOAc—CH$_2$Cl$_2$-hexane.

Physical data: mp 126–127° C.
MS (EI) m/z 419 (M+).
Anal. calcd for $C_{16}H_{19}F_2N_3O_4S_2$: C, 45.81; H, 4.57; N, 10.02. Found: C, 45.47; H, 4.53; N, 9.93.

Example 17

Preparation of 2,2-difluoro-N-({(5S)-3-[4-(1-oxidothiomorpholin-4-yl)phenyl]-2-oxo-1,3-oxazolidin-5-yl}methyl)ethanethioamide (36)

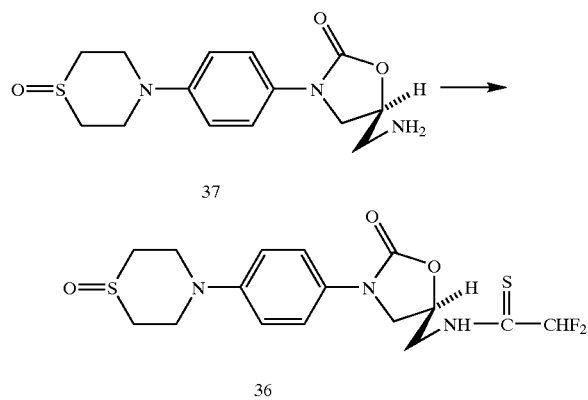

Following the procedure described in Example 10 for the preparation of 22, the reaction of 37 (prepared according to the procedure described in U.S. Pat. No. 6,342,523) with 7 provides the title compound 36 which is crystallized from EtOAc-hexan.

Physical data: mp 155–156° C.
MS (EI) m/z 403.1 (M+).
Anal. calcd for $C_{16}H_{19}F_2N_3O_2S_2$: C, 47.63; H, 4.75; N, 10.41. Found: C, 47.64; H, 4.81; N, 10.31.

Example 18

Preparation of 2,2-difluoro-N-({(5S)-3-[3-fluoro-4-(1-imino-1-oxido-1$\lambda^4$, 4-thiazinan-4-yl)phenyl]-2-oxo-1,3-oxazolidin-5-yl}methyl)ethanethioamide (38,)

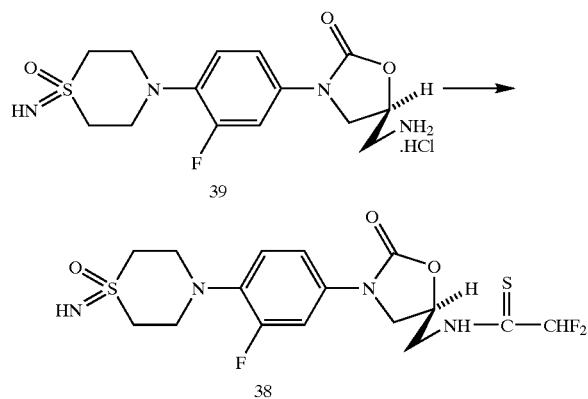

Following the procedure described in Example 14 for the preparation of 30, the reaction of 39 (prepared according to the procedure described in U.S. Pat. No. 6,342,523) and triethylamine in $CH_2Cl_2$ with 7 provides the title compound 38 which is purified by silica gel chromatography with 4% MeOH-0.5% $NH_4OH$—$CHCl_3$ and crystallization from MeOH.

Physical data: mp 199.5–200.0° C.
MS (ESI+) m/z 437 (M+H+).
MS (ESI-) m/z 435 (M-H).
Anal. calcd for $C_{16}H_{19}F_3N_4O_3S_2$: C, 44.03; H, 4.39; N, 12.84. Found: C, 44.02; H, 4.51; N, 12.68.

Example 19

Preparation of 2,2-difluoro-N-({(5S)-3-[3-fluoro-4-(1-oxido-1,4-thiazepan-4-yl)phenyl]-2-oxo-1,3-oxazolidin-5-yl}methyl)ethanethioamide (40)

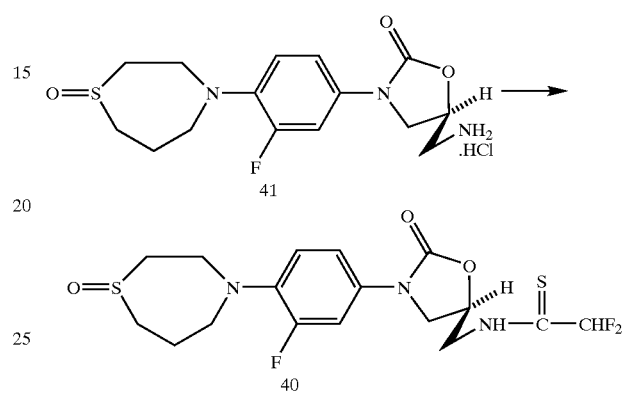

Following the procedure described in Example 10 for the preparation of 22, the reaction of 41 (prepared according to the procedure described in U.S. Pat. No. 6,342,523) with 7 provides 40 which is purified by silica gel chromatography with 2.5% MeOH—$CH_2Cl_2$.

Physical data: Anal. calcd for $C_{17}H_{20}F_3N_3S_2$: C, 46.89; H, 4.63; N, 9.65; S, 14.72. Found: C, 46.29; H, 4.92; N, 9.08; S, 13.76.

Example 20

Preparation of 2,2-difluoro-N-({(5S)-3-[4-(1-imino-1-oxido-1$\lambda^4$, 4-thiazinan-4-yl)phenyl]-2-oxo-1,3-oxazolidin-5-yl}methyl)ethanethioamide (42)

Step 1.

Preparation of N-({(5S)-3-[4-(1-oxidothiomorpholin-4-yl)phenyl]-2-oxo-1,3-oxazolidin-5-yl}methyl)acetamide (44)

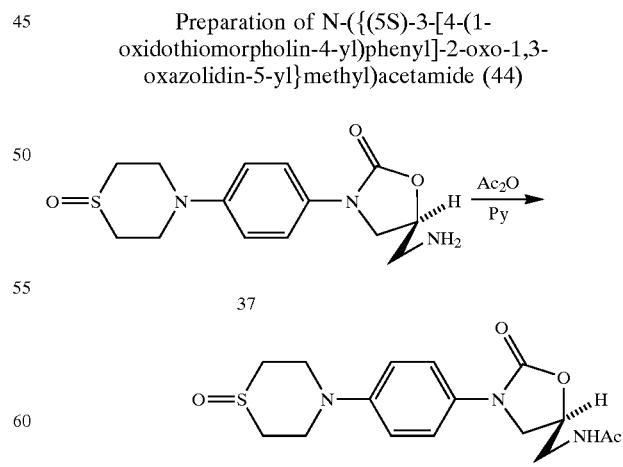

A stirred solution of 37 (prepared according to the procedure described in U.S. Pat. No. 6,342,523) (674 mg, 2.18 mmol) in pyridine (37 ml) is treated with acetic anhydride (308 µL, 3.27 mmol), kept at ambient temperature (about 24° C.) for 45 min and concentrated in vacuo. Chromatography of the residue on silica gel with 5% MeOH—CH$_2$Cl$_2$ and crystallization of the product from EtOAc-hexane provides the title compound 44, as solid: mp 185–186° C.; MS (EI) m/z 351.2 (M$^+$). Anal. calcd for C$_{16}$H$_{21}$N$_3$O$_4$S: C, 54.68; H, 6.02; N, 11.96. Found: C, 54.40; H, 6.01; N, 11.77.

Step 2.

Preparation of (5S)-5-(aminomethyl)-3-[4-(1-imino-1-oxido-1λ$^4$, 4-thiazinan-4-yl)phenyl]-1,3-oxazolidin-2-one hydrochloride (45)

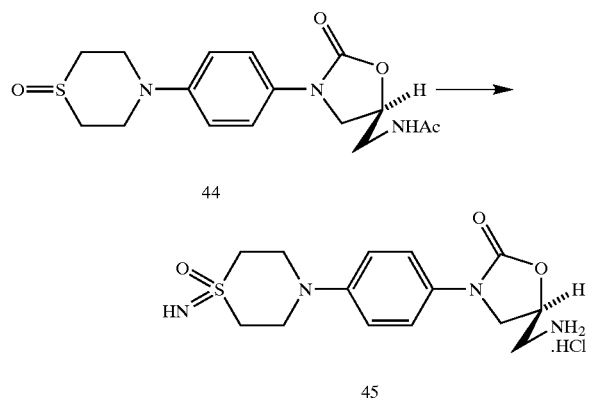

As described in International Publication WO 01/46185), the reaction of 44 with sodium azide in polyphosphonic acid provides N-({(5S)-3-[4-(1-imino-1-oxido-1λ$^4$, 4-thiazinan-4-yl)phenyl]-2-oxo-1,3-oxazolidin-5-yl}methyl)acetamide (47, see Example 21) which is hydrolyzed with 6N HCl in MeOH as described in Example 3 for the preparation of 10 to give the title compound 45.

Step 3.

Preparation of 2,2-difluoro-N-({(5S)-3-[4-(1-imino-1-oxido-1λ$^4$, 4-thiazinan-4-yl)phenyl]-2-oxo-1,3-oxazolidin-5-yl}methyl)ethanethioamide (42)

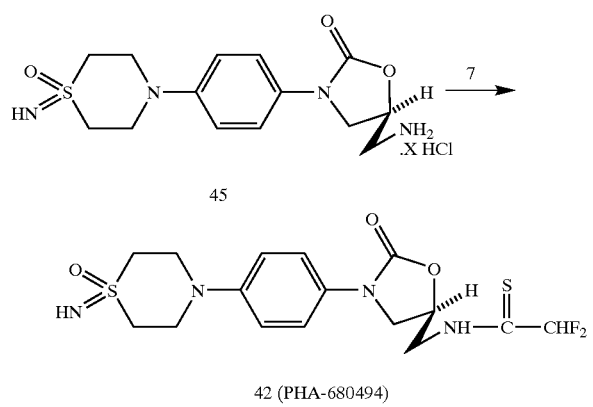

42 (PHA-680494)

Following the procedure described in Example 3, the reaction of 45 with 7 provides 42 which is purified by silica gel chromatography with 5% MeOH—CH$_2$Cl$_2$ and crystallization from MeOH—EtOAc.

Physical data: mp 182–183° C.

Anal calcd for C$_{16}$H$_{20}$F$_2$N$_4$O$_3$S$_2$: C, 45.92; H, 4.82; N, 13.39. Found: C, 45.43; H, 4.88; N, 13.23.

Example 21

Preparation of 2,2-difluoro-N-(((5S)-3-{4-[1-(methylimino)-1-oxido-1λ$^4$, 4-thiazinan-4-yl]phenyl}-2-oxo-1,3-oxazolidin-5-yl)methyl]ethanethioamide (46)

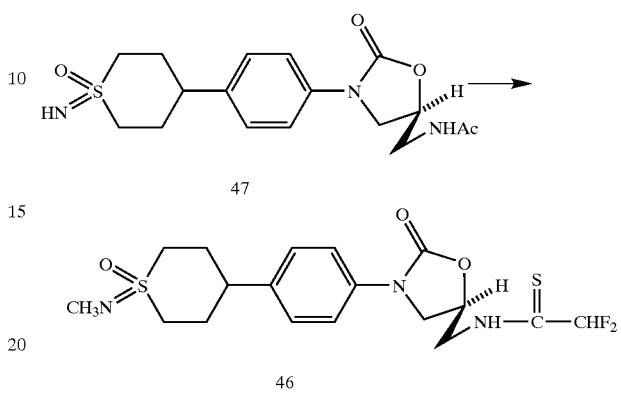

Following the procedure described in Example 4 for the preparation of 11, the reaction of 47 (prepared according to the procedure described in the International Publication WO 01/46185) with paraformaldehyde, triethylsilane and trifluoroacetic acid gave N-({(5S)-3-[4-(1-methylimino-1-oxido-1λ$^4$, 4-thiazinan-4-yl)phenyl]-2-oxo-1,3-oxazolidin-5-yl}methyl)acetamide (48) which is hydrolyzed with 6N HCl in MeOH. The reaction of the resulting product with 7 and triethylamine as described in Example 3 for the preparation of 8 provides the title compound 46 which is purified by silica gel chromatography with 5% MeOH—CH$_2$Cl$_2$ and crystallization from EtOAc—MeOH-hexane.

Physical data: mp 147–148° C.

MS (EI) m/z 432 (M$^+$).

Anal. calcd for C$_{17}$H$_{22}$F$_2$N$_4$O$_3$S$_2$: C, 47.21; H, 5.13; N, 12.95. Found: C, 47.23; H, 5.20; N, 12.97.

Example 22

Preparation of 2,2-difluoro-N-({(5S)-3-[3-fluoro-4-(1-oxidotetrahydro-2H-thiopyran-4-yl)phenyl]-2-oxo-1,3-oxazolidin-5-yl}methyl)ethanethioamide, E-Isomer (49). PNU-280711

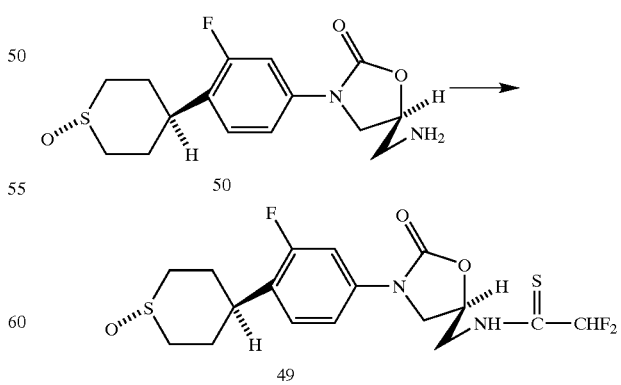

Following the procedure described in Example 9 for the preparation of 20, the reaction of 50 (prepared according to the procedure described in U.S. Pat. No. 6,342,523) with 7 provides 49 which is purified by silica gel chromatography with 3% MeOH—CH$_2$Cl$_2$.

Physical data: mp 192–194° C.

Anal. calcd for C$_{17}$H$_{19}$F$_3$N$_2$O$_3$S$_2$: C, 48.56; H, 4.55; N, 6.66; S, 15.25. Found: C, 48.30; H, 4.58; N, 6.41; S, 14.73.

Example 23

Preparation of 2,2-difluoro-N-({(5S)-3-[4-(1,1-dioxidotetrahydro-2H-thiopyran-4-yl)phenyl]-2-oxo-1,3-oxazolidin-5-yl}methyl)ethanethioamide (51)

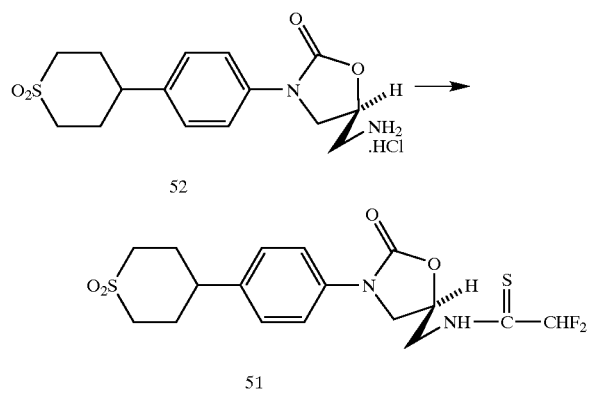

Condensation of 52 (prepared according to the procedure described in U.S. Pat. No. 6,342,523) with 7 and triethylamine in CH$_2$Cl$_2$ as described in Example 3 for the preparation of 8 provides 51 which is purified by silica gel chromatography with 2.5% MeOH—CHCl$_3$ and crystallization from MeOH.

Physical data: mp 174–176° C.

Anal calcd for C$_{17}$H$_{20}$F$_2$N$_2$O$_4$S$_2$: C, 48.79; H, 4.82; N, 6.69. Found: C, 47.95; H, 4.89; N, 6.43.

Example 24

Preparation of 2,2-difluoro-N-({(5S)-3-[4-(1-oxidotetrahydro-2H-thiopyran-4-yl)phenyl]-2-oxo-1,3-oxazolidin-5-yl}methyl)ethanethioamide, Z-isomer (53)

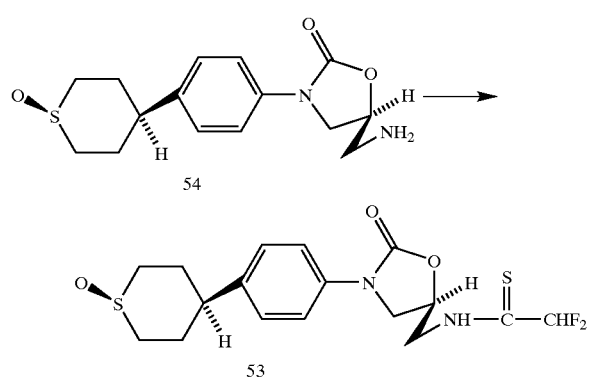

Condensation of 54 (prepared according to the procedure described in U.S. Pat. No. 6,342,523) with 7 and triethylamine in CH$_2$Cl$_2$ as described in Example 3 for the preparation of 8 provides the title compound 53 which is purified by silica gel chromatography with 2.5% MeOH—CH$_2$Cl$_2$ and crystallization from MeOH.

Physical data: mp 216–217° C. (dec.).

Anal. calcd for C$_{17}$H$_{20}$F$_2$N$_2$O$_3$S$_2$: C, 50.73; H, 5.01; N, 6.96. Found: C, 50.75; H, 5.03; N, 6.96.

Example 25

Preparation of 2,2-difluoro-N-({(5S)-3-[3,5-difluoro-4-(1-oxidotetrahydro-2H-thiopyran-4-yl)phenyl]-2-oxo-1,3-oxazolidin-5-yl}methyl)ethanethioamide, E-isomer (55)

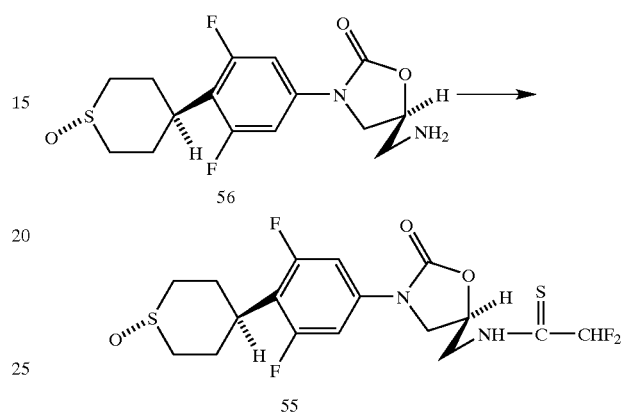

Condensation of 56 (prepared according to the procedure described in U.S. Pat. No. 6,342,523) with 7 and triethylamine in CH$_2$Cl$_2$ as described in Example 3 for the preparation of 8 provides the title compound 55.

Physical data: mp 102° C. (dec).

HRMS calcd for C$_{17}$H$_{19}$F$_4$N$_2$O$_3$S$_2$ (M+H$^+$) 439.0773, found 439.0795.

Anal. calcd for C$_{17}$H$_{18}$F$_4$N$_2$O$_3$S$_2$: C, 46.57; H, 4.14; N, 6.39. Found: C, 46.12; H, 4.26; N, 5.69.

Example 26

Preparation of 2,2-difluoro-N-({(5S)-3-[4-(1-oxidotetrahydro-2H-thiopyran-4-yl)phenyl]-2-oxo-1,3-oxazolidin-5-yl}methyl)ethanethioamide, E-isomer (57)

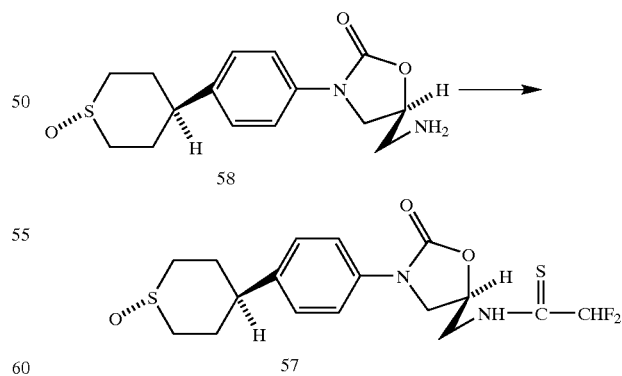

Condensation of 58 (prepared according to the procedure described in U.S. Pat. No. 6,342,523) with 7 and triethylamine in CH$_2$Cl$_2$ as described in Example 3 for the preparation of 8 provides the title compound 57 which is crystallized from MeOH.

Physical data: mp 212–213° C. (dec.).

Anal. calcd for $C_{17}H_{20}F_2N_2O_3S_2$: C, 50.73; H, 5.01; N, 6.96. Found: C, 50.55; H, 5.08; N, 6.88.

Example 27

Preparation of 2,2-difluoro-N-({(5S)-3-[3,5-difluoro-4-(1-oxidotetrahydro-2H-thiopyran-4-yl)phenyl]-2-oxo-1,3-oxazolidin-5-yl}methyl)ethanethioamide, Z-isomer (59)

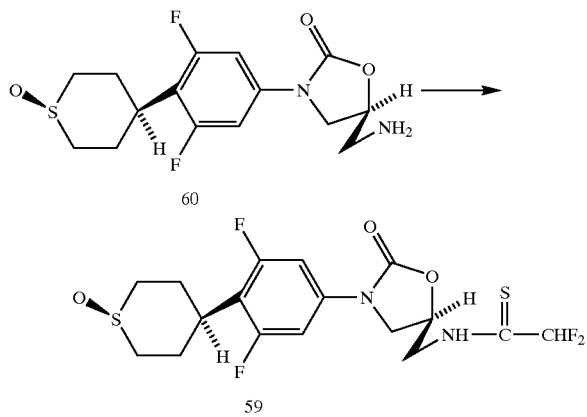

Condensation of 60 (prepared according to the procedure described in U.S. Pat. No. 6,342,523) with 7 and triethylamine in DMF as described in Example 3 for the preparation of 8 provides the title compound 59.

Physical data: mp 219–221° C.

HRMS calcd for $C_{17}H_{19}F_4N_2O_3S_2$ (M+H$^+$) 439.0773, found 439.0772.

Anal. calcd for $C_{17}H_{18}F_4N_2O_3S_2$: C, 46.57; H, 4.14; N, 6.39. Found: C, 46.49; H, 4.18; N, 6.36.

Example 28

Preparation of 2,2-difluoro-N-({(5S)-3-[4-(1-imino-1-oxidohexahydro-1λ$^4$-thiopyran-4-yl)phenyl]-2-oxo-1,3-oxazolidin-5-yl}methyl)ethanethioamide, Z-isomer (61)

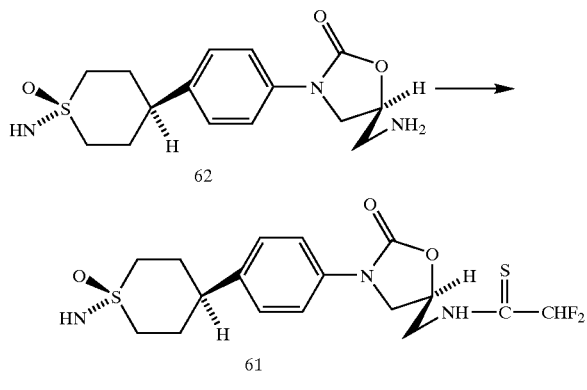

Condensation of 62 (prepared according to the procedure described in U.S. Pat. No. 6,342,523) with 7 and triethylamine in CH$_2$Cl$_2$ as described in Example 3 for the preparation of 8 provides the title compound 61 which is purified by silica gel chromatography with 4% MeOH—CHCl$_3$ and crystallization from MeOH.

Physical data: mp 188–189° C.

MS (ESI+) m/z 418 (M+H$^+$); MS (ESI–) m/z 416 (M–H).

Anal. calcd for $C_{17}H_{21}F_2N_3O_3S_2$: C, 48.91; H, 5.07; N, 10.06. Found: C, 48.73; H, 5.09; N, 9.93.

Example 29

Preparation of 2,2-difluoro-N-({(5S)-3-[4-(1-imino-1-oxidohexahydro-1λ$^4$-thiopyran-4-yl)phenyl]-2-oxo-1,3-oxazolidin-5-yl}methyl)ethanethioamide, E-isomer (63)

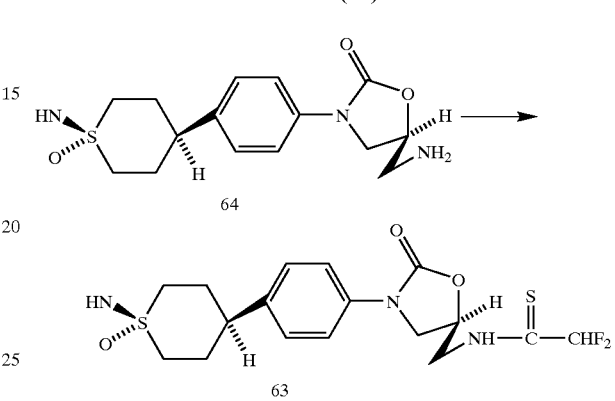

Condensation of 64 (prepared according to the procedure described in U.S. Pat. No. 6,342,523) with 7 and triethylamine in CH$_2$Cl$_2$ as described in Example 3 for the preparation of 8 provides the title compound 63 which is purified by silica gel chromatography with 3.5% MeOH—CH$_2$Cl$_2$ and crystallization from MeOH.

Physical data: mp 184–185° C. (dec).

MS (ESI+) m/z 418 (M+H$^+$), 440 (M+Na$^+$).

MS (ESI–) m/z 416 (M–H).

Anal. calcd for $C_{17}H_{21}F_2N_3O_3S_2$: C, 48.91; H, 5.07; N, 10.06. Found: C, 48.80; H, 5.09; N, 10.00.

Example 30

Preparation of 2,2-difluoro-N-({(5S)-3-[4-(1-methylimino-1-oxidohexahydro-1λ$^4$-thiopyran-4-yl)phenyl]-2-oxo-1,3-oxazolidin-5-yl}methyl)ethanethioamide, Z-isomer (65)

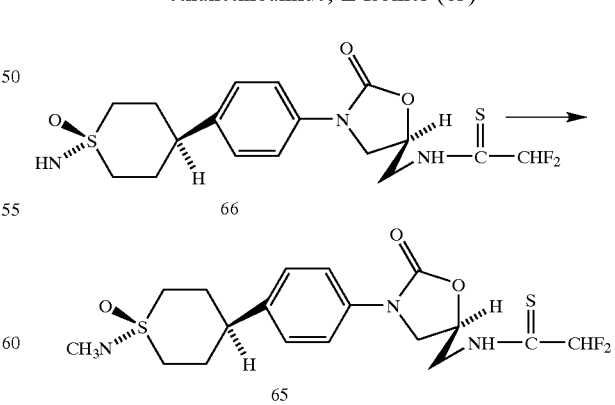

Following the procedure described in Example 4 for the preparation of 11 the reaction of 66 (prepared according to the procedure described in U.S. Pat. No. 6,342,523) with paraformaldehyde, TFA, and triethylsilane provides the title compound 65 which is purified by silica gel chromatography eluting first with 50% CH$_3$CN—CH$_2$Cl$_2$ and then with 5% MeOH—CHCl$_3$.

Physical data: HRMS (FAB) calcd for C$_{18}$H$_{24}$F$_2$N$_3$O$_3$S$_2$ (M+H$^+$) 432.1227, found 432.1239.

Anal. calcd for C$_{18}$H$_{23}$F$_2$N$_3$O$_3$S$_2$: C, 50.10; H, 5.37; N, 9.74. Found: C, 50.15; H, 5.53; N, 9.48.

Example 31

Preparation of 2,2-difluoro-N-({(5S)-3-[4-(1-methylimino-1-oxidohexahydro-1λ$^4$-thiopyran-4-yl)phenyl]-2-oxo-1,3-oxazolidin-5-yl}methyl)ethanethioamide, E-isomer (67)

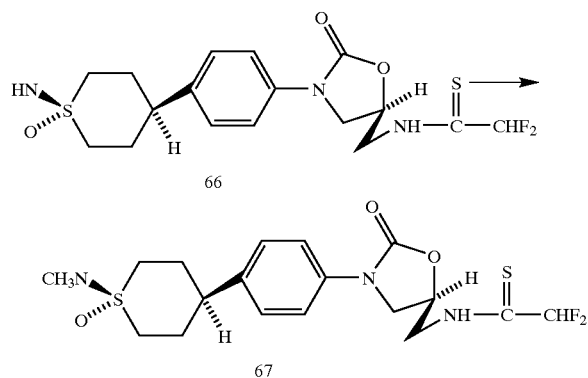

Following the procedure described in Example 4 for the preparation of 11 the reaction of 68 (prepared according to the procedure described in U.S. Pat. No. 6,342,523) with paraformaldehyde, TFA, and triethylsilane provides the title compound 83 which is purified by silica gel chromatography first with 50% CH$_3$CN—CH$_2$Cl$_2$ and a second time with 4% MeOH—CHCl$_3$.

Physical data: HRMS (FAB) calcd for C$_{18}$H$_{24}$F$_2$N$_3$O$_3$S$_2$ (M+H$^+$) 432.1227, found 432.1239.

Anal. calcd for C$_{18}$H$_{23}$F$_2$N$_3$O$_3$S$_2$: C, 50.10; H, 5.37; N, 9.74. Found: C, 50.09; H, 5.52; N, 9.43.

Pharmaceutical Salts

The compound of formula I may be used in its native form or as a salt. In cases where forming a stable nontoxic salt is desired, administration of the compound as a pharmaceutically acceptable salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, hydrobromide, sulfate, nitrate, bicarbonate, and carbonate salts. Pharmaceutically acceptable salts may be obtained using standard procedures well known in the art, for example by reacting a compound of the present invention with a suitable acid affording a physiologically acceptable anion.

Doses for Individual/Combination Therapy

In combating the infective diseases caused by gram-positive organisms, the compound of the formula I can be used either individually, or in combination with other antibiotics that are active against gram-positive organisms. Some of the gram-positive antibiotics may also have activity against gram-negative organisms.

Examples of such gram-positive antibiotics are listed in Table 1.

TABLE 1

Gram-Positive Antibiotics That May Be Used In a Combination Therapy With The Compound of Formula I

| AGENTS | LO DOSE | HI DOSE | STD DOSE |
|---|---|---|---|
| AMINOGLYCOSIDES | | | |
| Amikacin | | | 15 mg/kg/day |
| Gentamicin | 1 mg/kg/day | 5 mg/kg/day | |
| | .5 mg/kg | 2.5 mg/kg | |
| Spectinomycin | | | 40 mg/kg |
| Tobramycin | 1 mg/kg/day | 5 mg/kg/day | |
| | .5 mg/kg/day | 5 mg/kg/day | |
| PENEMS | | | |
| Imipenem/cilastatin | 62.5 mg | 1 g | |
| | 6.25 mg/kg | 25 mg/kg | |
| Meropenem | | | 40 mg/kg |
| | .5 mg/kg | 2.5 mg/kg | |
| 1$^{ST}$ GEN CEPHS | | | |
| Cefadroxil | .25 g/day | 2 g/day | |
| | | | 30 mg/kg/day |
| Cefazolin | 62.5 mg | 1.5 g | |
| | 6.25 mg/kg/day | 100 mg/kg/day | |
| Cephalexin | 62.5 mg | 500 mg | |
| | 6.25 mg/kg/day | 50 mg/kg/day | |
| 2$^{ND}$ GEN CEPHS | | | |
| Cefaclor | 62.5 mg | 500 mg | |
| | 5 mg/kg/day | 40 mg/kg/day | |
| Cefotetan | 0.125 g | 3 g | |
| | 10 mg/kg/day | 80 mg/kg/day | |

TABLE 1-continued

Gram-Positive Antibiotics That May Be Used
In a Combination Therapy With The Compound of Formula I

| AGENTS | LO DOSE | HI DOSE | STD DOSE |
|---|---|---|---|
| Cefoxitin | .25 g | 3 g | |
| | 20 mg/kg/day | 160 mg/kg/day | |
| Cefprozil | 62.5 mg | 500 mg | |
| | 1.87 mg/kg/dose | 15 mg/kg/dose | |
| Cefuroxime | 187.5 mg | 3 g | |
| | 31.25 mg | 500 mg | |
| | 12.5 mg/kg/day | 150 mg/kg/day | |
| | 31.25 mg/kg/day | 500 mg/kg/day | |
| Loracarbef | 50 mg | 400 mg | |
| | 3.75 mg/kg/day | 500 mg/kg/day | |
| $3^{RD}$ GEN CEPHS | | | |
| Cefdinir | 75 mg | | 600 mg |
| Cefixime | 50 mg | | 400 mg |
| Cefoperazone | .5 g/day | 12 g/day | |
| | 25 mg/kg/day | 150 mg/kg/day | |
| Cefotaxime | .25 g | 2 g | |
| | 12.5 mg/kg/dose | 300 mg/kg/day | |
| Cefpodoxime | 25 mg | 400 mg | 10 mg/kg/day |
| Ceftazidime | 62.5 mg | 2 g q8 | |
| | 25 mg/kg/day | 150 mg/kg/day | |
| Ceftibuten | 2.25 mg/kg | 400 mg | 400 mg |
| Ceftozoxime | .25 g | 4 g | |
| | 12.5 mg/kg/day | 200 mg/kg/day | |
| Ceftriaxone | 31.25 mg | 2 g | |
| | 12.5 mg/kg/day | 100 mg/kg/day | |
| $4^{TH}$ GEN CEPHS | | | |
| Cefepime | 0.125 g | 2 g | |
| | 12.5 mg/kg | 50 mg/kg q8 | |
| MACROLIDES | | | |
| Azithromycin | 62.5 mg | 500 mg | |
| | 62.5 mg | 500 mg | |
| Clarithromycin | 62.5 mg | 500 mg | 7.5 mg/kg/day |
| Dirithromycin | | | 500 mg |
| $1^{ST}$ GEN PENS | | | |
| Penicillin G | 2 million units/day | 30 million units/day | |
| | 2000 units/kg/dy | 400,000 units/kg/day | |
| $2^{ND}$ GEN PENS | | | |
| Cloxacillin | 62.5 mg | 500 mg | |
| | 12.5 mg/kg/day | 100 mg/kg/day | |
| Dicloxacillin | 31.25 mg | 500 mg | |
| | 3.125 mg/kg/day | 100 mg/kg/day | |
| Nafcillin | 125 mg | 2 g | |
| | 2.5 mg/kg | 25 mg/kg | |
| Oxacillin | 62.5 mg | 2 g | |
| | 125 mg | 1000 mg | |
| | 25 mg/kg/day | 200 mg/kg/day | |
| | 12.5 mg/kg/day | 100 mg/kg/day | |
| $3^{RD}$ GEN PENS | | | |
| Amoxicillin | 62.5 mg | 875 mg | |
| | 5 mg/kg/day | 45 mg/kg | |
| Amoxicillin/clavulanic acid | 62.5 mg | 875 mg | |
| | 6.25 mg/kg/day | 45 mg/kg/day | |
| Ampicillin | 62.5 mg | 12 g/day q4 | |
| | 6.25 mg/kg/day | 300 mg/kg/day | |
| Ampicillin/sulbactam | 0.375 g | 3 g | 300 mg/kg/day |
| $4^{TH}$ GEN PENS | | | |
| Mezlocillin | 0.375 g | 4 g | 75 mg/kg |
| Piperacillin | 1.5 g/day | 24 g day | |
| | 25 mg/kg/day | 300 mg/kg/day | |
| Piperacillin/tazobactam | | | 240 mg/kg/day |
| Ticarcillin | .25 g | 4 g | |
| | 12.5 mg/kg/day | 300 mg/kg/day | |
| Ticarcillin/clavulanate | 50 mg/kg/day | 300 mg/kg/day | |
| | 0.775 g | 3.1 g | |
| $1^{ST}$ GEN QUINOLONES | | | |
| Nalidixic Acid | | | 55 mg/kg/day |

TABLE 1-continued

Gram-Positive Antibiotics That May Be Used
In a Combination Therapy With The Compound of Formula I

| AGENTS | LO DOSE | HI DOSE | STD DOSE |
|---|---|---|---|
| 2$^{ND}$ GEN QUINOLONES | | | |
| Ciprofloxacin | 50 mg | 750 mg | |
| | 2.5 mg/kg/dose | 15 mg/kg/dose | |
| | 62.5 mg | 750 mg | |
| | 2.5 mg/kg/dose | 15 mg/kg/dose | |
| Enoxacin | 50 mg | 400 mg | |
| Lomefloxacin | | | 400 mg |
| Norfloxacin | | | 400 mg |
| Ofloxacin | 50 mg | 400 mg | |
| 3$^{RD}$ GEN QUINOLONES | | | |
| Levofloxacin | 62.5 mg | 750 mg | |
| Sparfloxacin | 50 mg | 400 mg | |
| 4$^{TH}$ GEN QUINOLONES | | | |
| Alatrofloxacin | 50 mg | 300 mg | |
| Gatifloxacin | 50 mg | 400 mg | |
| Moxifloxacin | | | 400 mg |
| SULFAS | | | |
| Trimethoprim/sulfamethoxazole | 15 mg | 800 mg | |
| | 3.75 mg/day | 150 mg/day | |
| Sulfisoxazole | 18.75 mg | 150 mg | |
| Sulfamethoxazole | .25 g | 2 g | |
| TETRACYCLINES | | | |
| Doxycycline | 5 mg | 100 mg | |
| Minocycline | 25 mg | 200 mg | |
| Tetracycline | 62.5 mg | 500 mg | |
| OTHER | | | |
| Chloramphenicol | 12.5 mg/kg/day | 100 mg/kg/day | |
| Clindamycin | 150 mg | 900 mg | |
| | 37.5 mg | 450 mg | |
| | 5 mg/kg/day | 40 mg/kg/day | |
| | 2 mg/kg/day | 25 mg/kg/day | |
| Quinupristin/dalfopristin | 1.875 mg/kg | 7.5 mg/kg q8 | |
| Fosfomycin | | | 3 g |
| Nitrofurantoin | 12.5 mg | 100 mg | |
| | 1.25 mg/kg/day | 7 mg/kg/day | |
| Rifampin | 2.5 mg/kg | 600 mg/kg | |
| | 2.5 mg/kg | 600 mg/kg | |
| Trimethoprim | 25 mg | 200 mg | 10 mg/kg/day |
| Vancomycin | | | 1 g |
| | 2.5 mg/kg q6 | 15 mg/kg q8 | |

In combating the infective diseases caused by gram-positive and gram-negative organisms, the compound of the formula I can be used in combination with other antibiotics that are active against gram-negative organisms. Examples of such gram-negative antibiotics are listed in Table 2. Some of gram-negative antibiotics may also have activity against gram-positive organisms.

TABLE 2

Gram-Negative Antibiotics That May Be Used
In a Combination Therapy with The Compound of Formula I

| AGENTS | LO DOSE | HI DOSE | STD DOSE |
|---|---|---|---|
| AMINO-GLYCOSIDES | | | |
| Amikacin | | 15 mg/kg/day | |
| Gentamicin | 0.75 mg/kg/day | 5 mg/kg/day | |
| | 0.5 mg/kg | 2.5 mg/kg | |
| Spectinomycin | | | 40 mg/kg |

TABLE 2-continued

Gram-Negative Antibiotics That May Be Used
In a Combination Therapy with The Compound of Formula I

| AGENTS | LO DOSE | HI DOSE | STD DOSE |
|---|---|---|---|
| Tobramycin | 0.75 mg/kg/day | 5 mg/kg/day | |
| | 0.5 mg/kg/day | 5 mg/kg/day | |
| PENEMS | | | |
| Imipenem/cilastatin | 62.5 mg | 1 g | |
| | 6.25 mg/kg | 25 mg/kg | |
| Meropenem | | | 40 mg/kg |
| | 0.5 mg/kg | 2.5 mg/kg | |
| 2$^{ND}$ GEN CEPHS | | | |
| Cefaclor | 62.5 mg | 500 mg | |
| | 5 mg/kg/day | 40 mg/kg/day | |
| Cefotetan | 0.125 g | 3 g | |
| | 10 mg/kg/day | 80 mg/kg/day | |
| Cefoxitin | 0.25 g | 3 g | |
| | 20 mg/kg/day | 160 mg/kg/day | |

TABLE 2-continued

Gram-Negative Antibiotics That May Be Used
In a Combination Therapy with The Compound of Formula I

| AGENTS | LO DOSE | HI DOSE | STD DOSE |
|---|---|---|---|
| Cefprozil | 62.5 mg | 500 mg | |
| | 1.875 mg/kg/dose | 15 mg/kg/dose | |
| Cefuroxime | 187.5 mg | 3 g | |
| | 31.25 mg | 500 mg | |
| | 12.5 mg/kg/day | 150 mg/kg/day | |
| | 31.25 mg/kg/day | 500 mg/kg/day | |
| Loracarbef | 50 mg | 400 mg | |
| | 3.75 mg/kg/day | 500 mg/kg/day | |
| 3$^{RD}$ GEN CEPHS | | | |
| Cefdinir | 75 mg | | 600 mg qd |
| Cefixime | 50 mg | | 400 mg |
| Cefoperazone | 0.25 g/day | 12 g/day | |
| | 25 mg/kg/day | 150 mg/kg/day | |
| Cefotaxime | 0.25 g | 2 g | |
| | 12.5 mg/kg/dose | 300 mg/kg/day | |
| Cefpodoxime | 25 mg | 400 mg | 10 mg/kg/day |
| Ceftazidime | 62.5 mg | 2 g q8 | |
| | 25 mg/kg/day | 150 mg/kg/day | |
| Ceftibuten | 2.25 mg/kg | 400 mg | 400 mg |
| Ceftozoxime | 0.25 g | 4 g | |
| | 12.5 mg/kg/day | 200 mg/kg/day | |
| Ceftriaxone | 31.25 mg | 2 g | |
| | 12.5 mg/kg/day | 100 mg/kg/day | |
| 4$^{TH}$ GEN CEPHS | | | |
| Cefepime | 0.125 g | 2 g | |
| | 12.5 mg/kg | 50 mg/kg q8 | |
| MACROLIDES | | | |
| Azithromycin | 62.5 mg | 500 mg | |
| | 62.5 mg | 500 mg | |
| Clarithromycin | 62.5 mg | 500 mg | 7.5 mg/kg/day |
| Dirithromycin | | | 500 mg |
| 3$^{RD}$ GEN PENS | | | |
| Amoxicillin | 62.5 mg | 875 mg | |
| | 5 mg/kg/day | 45 mg/kg | |
| Amoxicillin/ | 62.5 mg | 875 mg | |
| clavulanic acid | 6.25 mg/kg/day | 45 mg/kg/day | |
| Ampicillin | 62.5 mg | 12 g/day q4 | |
| | 6.25 mg/kg/day | 300 mg/kg/day | |
| Ampicillin/ | 0.375 g | 3 g | 300 mg/kg/day |
| sulbactam | | | |
| 4$^{TH}$ GEN PENS | | | |
| Mezlocillin | 0.375 g | 4 g | 75 mg/kg |
| Piperacillin | 1.5 g/day | 24 g day | |
| | 25 mg/kg/day | 300 mg/kg/day | |
| Piperacillin/ | | | 240 mg/kg/day |
| tazobactam | | | |
| Ticarcillin | 0.25 g | 4 g | |
| | 12.5 mg/kg/day | 300 mg/kg/day | |
| Ticarcillin/ | 50 mg/kg/day | 300 mg/kg/day | |
| clavulanate | 0.775 g | 3.1 g | |
| 1$^{ST}$ GEN QUINOLONES | | | |
| Nalidixic Acid | | | 55 mg/kg/day |
| 2$^{ND}$ GEN QUINOLONES | | | |
| Ciprofloxacin | 50 mg | 750 mg | |
| | 2.5 mg/kg/dose | 15 mg/kg/dose | |
| | 62.5 mg | 750 mg | |
| | 2.5 mg/kg/dose | 15 mg/kg/dose | |
| Enoxacin | 50 mg | 400 mg | |
| Lomefloxacin | | | 400 mg |
| Norfloxacin | | | 400 mg |
| Ofloxacin | 50 mg | 400 mg | |
| 3$^{RD}$ GEN QUINOLONES | | | |
| Levofloxacin | 62.5 mg | 750 mg | |
| Sparfloxacin | 50 mg | 400 mg | |
| 4$^{TH}$ GEN QUINOLONES | | | |
| Alatrofloxacin | 50 mg | 300 mg | |
| Gatifloxacin | 50 mg | 400 mg | |
| Moxifloxacin | | | 400 mg |
| SULFAS | | | |
| Trimethoprim/ sulfamethoxazole | 15/200 mg | | |
| | 3.75 mg/day | 150 mg/day | |
| Sulfisoxazole | 18.75 mg | 150 mg | |
| Sulfamethoxazole | 0.25 g | 2 g | |
| TETRACYCLINES | | | |
| Doxycycline | 5 mg | 100 mg | |
| Minocycline | 25 mg | 200 mg | |
| Tetracycline | 62.5 mg | 500 mg | |
| OTHER | | | |
| Chloramphenicol | 12.5 mg/kg/day | 100 mg/kg/day | |
| Aztreonam | 125 mg | 2 g | |
| | 37.5 mg | 450 mg | |
| | 5 mg/kg/day | 40 mg/kg/day | |
| | 2 mg/kg/day | 25 mg/kg/day | |
| Fosfomycin | | | 3 g |
| Nitrofurantoin | 12.5 mg | 100 mg | |
| | 1.25 mg/kg/day | 7 mg/kg/day | |
| | 2.5 mg/kg | 600 mg/kg | |
| Trimethoprim | 25 mg | 200 mg | 10 mg/kg/day |

In Tables 1 and 2, the term "Lo Dose" means the recommended lower dosage for the combination therapy of the invention. It may be adjusted even lower depending on the requirements of each subject being treated and the severity of the bacterial infection. The lowest dosage possible may be 0.1 mg when combined with the compound of formula I of the present invention. The term "Hi Dose" means the recommended highest dosage in the combination therapy. It may be changed hereafter according to the US FDA standard. The term "Std Dose" means the recommended standard dosage for the combination therapy of the present invention. It may be adjusted even lower depending on the requirements of each subject being treated and the severity of the bacterial infection. A specific antibiotic may have more than one the recommended dosage ranges.

Generally, an antibacterially effective amount of dosage of the compound of formula I of the present invention, either administered individually or in combination with other antibiotics, will be in the range of about 0.1 to about 400 mg/kg of body weight/day, more preferably about 1.0 to about 50 mg/kg of body weight/day. It is to be understood that the dosages of active component(s) may vary depending upon the requirements of each subject being treated and the severity of the bacterial infection. In average, the effective amount of an active component is about 20 mg to 800 mg and preferable is about 200 mg to 600 mg per day.

The desired dose may conveniently be presented in a single dose or as divided into multiple doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation.

In cases of local administration or selective uptake, the effective local concentration of the drug may not be related to plasma concentration and other procedures know in the art may be used to determine the desired dosage amount.

For the combination therapy, the compound of formula I may be administered concurrently or concomitantly with other antibiotics. The term "concurrently" means the subject being treated takes one drug within about 5 minutes of taking the other drug. The term "concomitantly" means the subject being treated takes one drug within the same treatment period of taking the other drug. The same treatment period is preferably within twelve hours and up to forty-eight hours.

For the combination therapy, the compound of formula I, and one or more other antibiotics may be administered in the same physical form or separately, i.e., they may be administered in the same delivery vehicle or in different delivery vehicles.

For the combination therapy, some of the antibiotics may further be used with a β-Lactamase inhibitor. For example, Imipenem may be used with cilastatin, Ampicillin may be used with sulbactam, Piperacillin may be used with tazobactam, and Ampicillin may be used with sulbactam.

Specifically, the combination therapy of the present invention is the compound of formula I of the present invention with Amikacin.

Specifically, the combination therapy of the present invention is the compound of formula I of the present invention with Gentamicin.

Specifically, the combination therapy of the present invention is the compound of formula I of the present invention with Spectinomycin.

Specifically, the combination therapy of the present invention is the compound of formula I of the present invention with Tobramycin.

Specifically, the combination therapy of the present invention is the compound of formula I of the present invention with Imipenem/cilastatin.

Specifically, the combination therapy of the present invention is the compound of formula I of the present invention with Meropenem.

Specifically, the combination therapy of the present invention is the compound of formula I of the present invention with Cefadroxil.

Specifically, the combination therapy of the present invention is the compound of formula I of the present invention with Cefazolin.

Specifically, the combination therapy of the present invention is the compound of formula I of the present invention with Cephalexin.

Specifically, the combination therapy of the present invention is the compound of formula I of the present invention with Cefaclor.

Specifically, the combination therapy of the present invention is the compound of formula I of the present invention with Cefotetan.

Specifically, the combination therapy of the present invention is the compound of formula I of the present invention with Cefoxitin.

Specifically, the combination therapy of the present invention is the compound of formula I of the present invention with Cefprozil.

Specifically, the combination therapy of the present invention is the compound of formula I of the present invention with Cefuroxime.

Specifically, the combination therapy of the present invention is the compound of formula I of the present invention with Loracarbef.

Specifically, the combination therapy of the present invention is the compound of formula I of the present invention with Cefdinir.

Specifically, the combination therapy of the present invention is the compound of formula I of the present invention with Cefixime.

Specifically, the combination therapy of the present invention is the compound of formula I of the present invention with Cefoperazone.

Specifically, the combination therapy of the present invention is the compound of formula I of the present invention with Cefotaxime.

Specifically, the combination therapy of the present invention is the compound of formula I of the present invention with Cefpodoxime.

Specifically, the combination therapy of the present invention is the compound of formula I of the present invention with Ceftazidime.

Specifically, the combination therapy of the present invention is the compound of formula I of the present invention with Ceftibuten.

Specifically, the combination therapy of the present invention is the compound of formula I of the present invention with Ceftozoxime.

Specifically, the combination therapy of the present invention is the compound of formula I of the present invention with Ceftriaxone.

Specifically, the combination therapy of the present invention is the compound of formula I of the present invention with Cefepime.

Specifically, the combination therapy of the present invention is the compound of formula I of the present invention with Azithromycin.

Specifically, the combination therapy of the present invention is the compound of formula I of the present invention with Clarithromycin.

Specifically, the combination therapy of the present invention is the compound of formula I of the present invention with Dirithromycin.

Specifically, the combination therapy of the present invention is the compound of formula I of the present invention with Penicillin G.

Specifically, the combination therapy of the present invention is the compound of formula I of the present invention with Cloxacillin.

Specifically, the combination therapy of the present invention is the compound of formula I of the present invention with Dicloxacillin.

Specifically, the combination therapy of the present invention is the compound of formula I of the present invention with Nafcillin.

Specifically, the combination therapy of the present invention is the compound of formula I of the present invention with Oxacillin.

Specifically, the combination therapy of the present invention is the compound of formula I of the present invention with Amoxicillin.

Specifically, the combination therapy of the present invention is the compound of formula I of the present invention with Amoxicillin/clavulanic acid.

Specifically, the combination therapy of the present invention is the compound of formula I of the present invention with Ampicillin.

Specifically, the combination therapy of the present invention is the compound of formula I of the present invention with Ampicillin/sulbactam.

Specifically, the combination therapy of the present invention is the compound of formula I of the present invention with Mezlocillin.

Specifically, the combination therapy of the present invention is the compound of formula I of the present invention with Piperacillin.

Specifically, the combination therapy of the present invention is the compound of formula I of the present invention with Piperacillin/tazobactam.

Specifically, the combination therapy of the present invention is the compound of formula I of the present invention with Ticarcillin.

Specifically, the combination therapy of the present invention is the compound of formula I of the present invention with Ticarcillin/clavulanate.

Specifically, the combination therapy of the present invention is the compound of formula I of the present invention with Nalidixic Acid.

Specifically, the combination therapy of the present invention is the compound of formula I of the present invention with Ciprofloxacin.

Specifically, the combination therapy of the present invention is the compound of formula I of the present invention with Enoxacin.

Specifically, the combination therapy of the present invention is the compound of formula I of the present invention with Lomefloxacin.

Specifically, the combination therapy of the present invention is the compound of formula I of the present invention with Norfloxacin.

Specifically, the combination therapy of the present invention is the compound of formula I of the present invention with Ofloxacin.

Specifically, the combination therapy of the present invention is the compound of formula I of the present invention with Levofloxacin.

Specifically, the combination therapy of the present invention is the compound of formula I of the present invention with Sparfloxacin.

Specifically, the combination therapy of the present invention is the compound of formula I of the present invention with Alatrofloxacin.

Specifically, the combination therapy of the present invention is the compound of formula I of the present invention with Gatifloxacin.

Specifically, the combination therapy of the present invention is the compound of formula I of the present invention with Moxifloxacin.

Specifically, the combination therapy of the present invention is the compound of formula I of the present invention with Trimethoprim/sulfamethoxazole.

Specifically, the combination therapy of the present invention is the compound of formula I of the present invention with Sulfisoxazole.

Specifically, the combination therapy of the present invention is the compound of formula I of the present invention with Sulfamethoxazole.

Specifically, the combination therapy of the present invention is the compound of formula I of the present invention with Doxycycline.

Specifically, the combination therapy of the present invention is the compound of formula I of the present invention with Minocycline.

Specifically, the combination therapy of the present invention is the compound of formula I of the present invention with Tetracycline.

Specifically, the combination therapy of the present invention is the compound of formula I of the present invention with Aztreonam.

Specifically, the combination therapy of the present invention is the compound of formula I of the present invention with Chloramphenicol.

Specifically, the combination therapy of the present invention is the compound of formula I of the present invention with Clindamycin.

Specifically, the combination therapy of the present invention is the compound of formula I of the present invention with Quinupristin/dalfopristin.

Specifically, the combination therapy of the present invention is the compound of formula I of the present invention with Fosfomycin.

Specifically, the combination therapy of the present invention is the compound of formula I of the present invention with Metronidazole.

Specifically, the combination therapy of the present invention is the compound of formula I of the present invention with Nitrofurantoin.

Specifically, the combination therapy of the present invention is the compound of formula I of the present invention with Rifampin.

Specifically, the combination therapy of the present invention is the compound of formula I of the present invention with Trimethoprim.

Specifically, the combination therapy of the present invention is the compound of formula I of the present invention with Vancomycin.

Routes of Administration

In therapeutic use for treating, or combating, bacterial infections in a mammal (i.e. human and animals) a compound of the present invention, its pharmaceutical compositions, or combining with other antibacterial agents can be administered orally, parenterally, topically, rectally, transmucosally, or intestinally.

Parenteral administrations include indirect injections to generate a systemic effect or direct injections to the afflicted area. Examples of parenteral administrations are subcutaneous, intravenous, intramuscular, intradermal, intrathecal, intraocular, intranasal, intravetricular injections or infusions techniques.

Topical administrations include the treatment of infectious areas or organs readily accessibly by local application, such as, for example, eyes, ears including external and middle ear infections, vaginal, open wound, skins including the surface skin and the underneath dermal structures, or other lower intestinal tract. Topical administrations also include transdermal delivery to generate a systemic effect.

The rectal administration includes the form of suppositories.

The transmucosal administration includes nasal aerosol or inhalation applications.

The preferred routes of administration are oral and parenteral.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions and the like, for oral ingestion by a patient. A carrier can be at least one substance which may also function as a diluent, flavoring agent, solubilizer, lubricant, suspending agent, binder, tablet disintegrating agent, and encapsulating agent. Examples of such carriers or excipients include, but are not limited to, magnesium carbonate, magnesium stearate, talc, sugar, lactose, sucrose, pectin, dextrin, mnnitol, sorbitol, starches, gelatin, cellulosic materials, low melting wax, cocoa butter or powder, polymers such as polyethylene glycols and other pharmaceutical acceptable materials.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identificatin or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, fi- or triglycerides. Stabilizers may be added in these formulations, also.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

The compounds may also be formulated for parenteral administration, e.g., by injections, bolus injection or continuous infusion. Formulations for parenteral administration may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

For injection, the compounds of the invention may be formulated in aqueous solution, preferably in physiologically compatible buffers or physiological saline buffer. Suitable buffering agents include trisodium orthophosphate, sodium bicarbonate, sodium citrate, N-methylglucamine, L(+)-lysine and L(+)-arginine.

Parenteral administrations also include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

For suppository administration, the compounds may also be formulated by mixing the agent with a suitable non-irritating excipient which is solid at room temperature but liquid at rectal temperature and therefore will melt in the rectum to release the drug. Such materials include cocoa butter, beeswax and other glycerides.

For administration by inhalation, compounds of the present invention can be conveniently delivered through an aerosol spray in the form of solution, dry powder, or suspensions. The aerosol may use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch.

For topical applications, the pharmaceutical composition may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion such as suspensions, emulsion, or cream containing the active components suspended or dissolved in one or more pharmaceutically acceptable carriers. Suitable carriers include, but are not limited to, mineral oil, sorbitan monostearate, polysorbate 60, cetyl esters wax, ceteary alcohol, 2-octyldodecanol, benzyl alcohol and water.

For ophthalmic and otitis uses, the pharmaceutical compositions may be formulated as micronized suspensions in isotonic, pH adjusted sterile saline, or preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

In addition to the formulations described previously, the compounds may also be formulated as depot preparations. Such long acting formulations may be in the forms of implants. A compound of this invention may be formulated for this route of administration with suitable biopolymers, hydrophobic materials, or as a sparing soluble derivative such as, without limitation, a sparingly soluble salt.

Additionally, the compounds may be delivered using a sustained-release system. Various sustained-release materials have been established and are well known by those skilled in the art. Sustained-release capsules may, depending on their chemical nature, release the compounds for 24 hours up to several days. Depending on the chemical natrue and the biological stability of the therapeutic reagent, additional strategies for protein stabilization may be employed.

The quantity of active component, that is the compound this invention, in the pharmaceutical composition and unit dosage form thereof may be varied or adjusted widely depending upon the manner of administration, the potency of the particular compound and the desired concentration. Determination of a therapeutically effective amount is well within the capability of those skilled in the art. Generally, the quantity of active component will range between 0.5% to 90% by weight of the composition.

We claim:

1. A compound of formula I

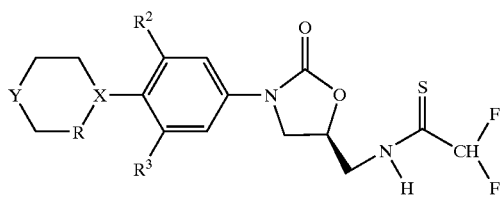

or pharmaceutically acceptable salt wherein
R is —CH₂— or —CH₂CH₂—;
R² and R³ are independently —H or —F;
X is —CH—;
Y is —SO—, —SO₂—, or —SONR⁴—; and R⁴ is —H or —C₁₋₄alkyl.

2. A compound of claim 1 wherein R² and R³ are H.
3. A compound of claim 1 wherein R² and R³ are F.
4. A compound of claim 1 wherein one of the R² and R³ is H, the other one is F.
5. A compound of claim 1 wherein R is —CH₂—.
6. A compound of claim 1 wherein X is CH.
7. A compound of claim 1 wherein Y is SO₂.
8. A compound of claim 1 wherein Y is SO.
9. A compound of claim 1 wherein Y is S(=O)NR⁴.
10. A compound of claim 9 wherein R⁴ is H or CH₃.
11. A compound of claim 1 which is a compound of formula Ia, Ib, Ic, or Id.

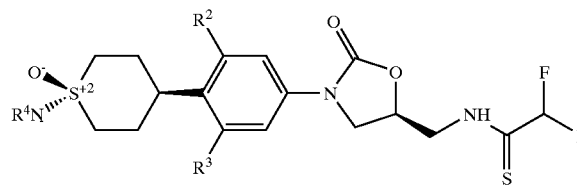

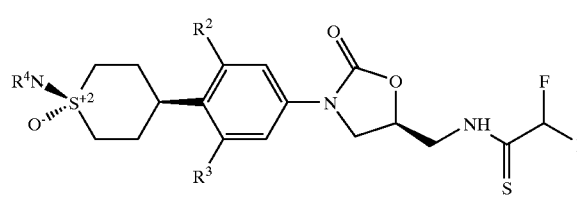

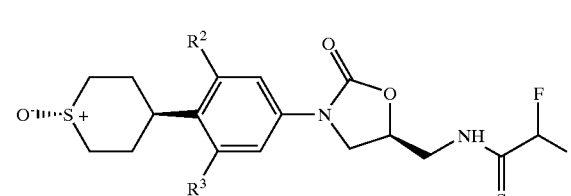

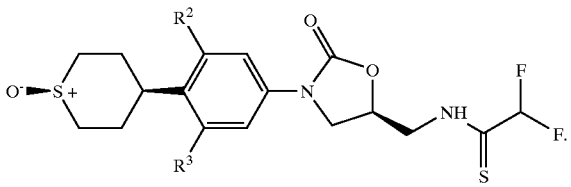

12. A method for treating bacteria infections comprising administering to a mammal being treated a pharmaceutically effective amount of the compound of claim 1.
13. The method of claim 12 wherein the compound of claim 1 is administered parenterally, topically, rectally, or intranasally.
14. The method of claim 12 wherein the compound of claim 1 is administered orally.
15. The method of claim 13 wherein parenteral administration is subcutaneous, intravenous, intramuscular, intradermal, intrathecal, intraocular, intravetricular injection.
16. The method of claim 13 wherein said compound is administered in an amount of from about 0.1 to about 100 mg/kg of body weight/day.
17. The method of claim 13 wherein said compound is administered in an amount of from about 1 to about 50 mg/kg of body weight/day.
18. The method of claim 12 wherein said infection is skin infection.
19. The method of claim 12 wherein the infection is eye infection.
20. The method of claim 12 wherein the infection is ear infection.
21. The method of claim 12 wherein said mammal is human.
22. The method of claim 12 wherein said mammal is an animal.
23. A pharmaceutical composition comprising the compound of claim 1 or its pharmaceutically acceptable salts thereof and a pharmaceutically acceptable carrier.
24. A compound of claim 1 which is
(1) 2,2-difluoro-N-({(5S-)-3-[3-fluoro-4-(1-imino-1-oxidohexahydro-1λ⁴-thiopyran-4-yl)phenyl]-2-oxo-1,3-oxazolidin-5-yl}methyl)ethanethioamide (Z-isomer),
(2) 2,2-difluoro-N-({(5S)-3-[3-fluoro-4-(1-imino-1-oxidohexahydro-1λ⁴-thiopyran-4-yl)phenyl]-2-oxo-1,3-oxazolidin-5-yl}methyl)ethanethioamide (E-isomer),
(3) 2,2-difluoro-N-({(5S)-3-[3-fluoro-4-(1-methylimino-1-oxidohexahydro-1λ⁴-thiopyran-4-yl)phenyl]-2-oxo-1,3-oxazolidin-5-yl}methyl)ethanethioamide (Z-isomer),
(4) 2,2-difluoro-N-({(5S)-3-[3-fluoro-4-(1-methylimino-1-oxidohexahydro-1λ⁴-thiopyran-4-yl)phenyl]-2-oxo-1,3-oxazolidin-5-yl}methyl)ethanethioamide (E-isomer),
(5) 2,2-difluoro-N-({(5S)-3-[4-(1,1-dioxidotetrahydro-2H-thiopyran-4-yl)-3-fluorophenyl]-2-oxo-1,3-oxazolidin-5-yl}methyl)ethanethioamide,
(6) 2,2-difluoro-N-({(5S)-3-[3-fluoro-4-(1-oxidotetrahydro-2H-thiopyran-4-yl)phenyl]-2-oxo-1,3-oxazolidin-5-yl}methyl)ethanethioamide (Z-Isomer),
(7) 2,2-difluoro-N-({(5S)-3-[4-(1,1-dioxidothiomorpholin-4-yl)-3,5-difluorophenyl]-2-oxo-1,3-oxazolidin-5-yl}methyl)ethanethioamide,
(8) 2,2-difluoro-N-({(5S)-3-[4-(1,1-dioxidotetrahydro-2H-thiopyran-4-yl)-3,5-difluorophenyl]-2-oxo-1,3-oxazolidin-5-yl}methyl)ethanethioamide,
(9) 2,2-difluoro-N-({(5S)-3-[3-fluoro-4-(1-oxidotetrahydro-2H-thiopyran-4-yl)phenyl]-2-oxo-1,3-oxazolidin-5-yl}methyl)ethanethioamide (E-Isomer),

(10) 2,2-difluoro-N-({(5S)-3-[4-(1,1-dioxidotetrahydro-2H-thiopyran-4-yl)phenyl]-2-oxo-1,3-oxazolidin-5-yl}methyl)ethanethioamide,
(11) 2,2-difluoro-N-({(5S)-3-[4-(1-oxidotetrahydro-2H-thiopyran-4-yl)phenyl]-2-oxo-1,3-oxazolidin-5-yl}methyl)ethanethioamide (Z-isomer),
(12) 2,2-difluoro-N-({(5S)-3-[3,5-difluoro-4-(1-oxidotetrahydro-2H-thiopyran-4-yl)phenyl]-2-oxo-1,3-oxazolidin-5-yl}methyl)ethanethioamide (E-isomer),
(13) 2,2-difluoro-N-({(5S)-3-[4-(1-oxidotetrahydro-2H-thiopyran-4-yl)phenyl]-2-oxo-1,3-oxazolidin-5-yl}methyl)ethanethioamide (E-isomer),
(14) 2,2-difluoro-N-({(5S)-3-[3,5-difluoro-4-(1-oxidotetrahydro-2H-thiopyran-4-yl)henyl]-2-oxo-1,3-oxazolidin-5-yl}methyl)ethanethioamide (Z-isomer),
(15) 2,2-difluoro-N-({(5S)-3-[4-(1-imino-1-oxidohexahydro-1$\lambda^4$-thiopyran-4-yl)phenyl]-2-oxo-1,3-oxazolidin-5-yl}methyl)ethanethioamide (Z-isomer),
(16) 2,2-difluoro-N-({(5S)-3-[4-(1-imino-1-oxidohexahydro-1$\lambda^4$-thiopyran-4-yl)phenyl]-2-oxo-1,3-oxazolidin-5-yl}methyl)ethanethioamide (E-isomer),
(17) 2,2-difluoro-N-({(5S)-3-[4-(1-methylimino-1-oxidohexahydro-1$\lambda^4$-thiopyran-4-yl)phenyl]-2-oxo-1,3-oxazolidin-5-yl}methyl)ethanethioamide (Z-isomer), or
(18) 2,2-difluoro-N-({(5S)-3-[4-(1-methylimino-1-oxidohexahydro-1-$\lambda^4$,4-thiopyran-4-yl)phenyl]-2-oxo-1,3-oxazolidin-5-yl}methyl)ethanethioamide (E-isomer).

* * * * *